(12) United States Patent
Shyu et al.

(10) Patent No.: US 9,540,611 B2
(45) Date of Patent: Jan. 10, 2017

(54) METHODS FOR TREATING AND/OR REVERSING NEURODEGENERATIVE DISEASES AND/OR DISORDERS

(75) Inventors: Woei-Cherng Shyu, TaiChung (TW); Shinn-Zong Lin, TaiChung (TW); Hsiao-Jung Wang, TaiChung (TW); Karl K. Johe, Potomac, MD (US)

(73) Assignee: Neuralstem, Inc., Germantown, MD (US)

( * ) Notice: Subject to any disclaimer, the term of this patent is extended or adjusted under 35 U.S.C. 154(b) by 0 days.

(21) Appl. No.: 13/192,972

(22) Filed: Jul. 28, 2011

(65) Prior Publication Data
US 2012/0177612 A1 Jul. 12, 2012

Related U.S. Application Data

(60) Provisional application No. 61/368,409, filed on Jul. 28, 2010.

(51) Int. Cl.
| | | |
|---|---|---|
| *C12N 5/0797* | (2010.01) | |
| *C12N 5/074* | (2010.01) | |
| *A01N 63/00* | (2006.01) | |
| *A61K 35/30* | (2015.01) | |

(52) U.S. Cl.
CPC .............. *C12N 5/0623* (2013.01); *A61K 35/30* (2013.01)

(58) Field of Classification Search
None
See application file for complete search history.

(56) References Cited

U.S. PATENT DOCUMENTS

| | | |
|---|---|---|
| 4,753,635 A | 6/1988 | Sagen et al. |
| 4,980,174 A | 12/1990 | Sagen et al. |
| 5,082,670 A | 1/1992 | Gage |
| 5,166,065 A | 11/1992 | Williams et al. |
| 5,175,103 A | 12/1992 | Lee et al. |
| 5,411,883 A | 5/1995 | Boss et al. |

(Continued)

FOREIGN PATENT DOCUMENTS

| | | |
|---|---|---|
| EP | 0 233 838 | 8/1987 |
| WO | WO 89/03872 | 5/1989 |

(Continued)

OTHER PUBLICATIONS

Daadi MM, Maag AL, Steinberg GK. "Adherent self-renewable human embryonic stem cell-derived neural stem cell line: functional engraftment in experimental stroke model." PLoS One. Feb. 20, 2008;3(2):e1644.*

(Continued)

*Primary Examiner* — Adam M Weidner
*Assistant Examiner* — Aurora M Fontainhas
(74) *Attorney, Agent, or Firm* — Morgan, Lewis & Bockius LLP; Christopher J. Betti (57) ABSTRACT

The present disclosure provides methods for the treatment of neurological diseases/disorders using neural stem cells (NSCs) obtained from a spinal cord tissue. The methods may include the use of a NSC population to treat a neurological disease/disorder of the brain. Such methods may include introducing exogenously cultured and expanded NSCs into the brain, which differentiate into neurons capable of integrating in vivo into the brain tissue in a sufficient manner to ameliorate the symptoms associated with the neurological disease/disorder.

23 Claims, 3 Drawing Sheets

(56) References Cited

U.S. PATENT DOCUMENTS

| | | | |
|---|---|---|---|
| 5,580,777 | A | 12/1996 | Bernard et al. |
| 5,589,376 | A | 12/1996 | Anderson et al. |
| 5,612,211 | A | 3/1997 | Wilson et al. |
| 5,672,499 | A | 9/1997 | Anderson et al. |
| 5,693,482 | A | 12/1997 | Anderson et al. |
| 5,750,376 | A | 5/1998 | Weiss et al. |
| 5,753,505 | A | 5/1998 | Luskin |
| 5,753,506 | A | 5/1998 | Johe |
| 5,770,414 | A | 6/1998 | Gage et al. |
| 5,824,489 | A | 10/1998 | Anderson et al. |
| 5,843,780 | A | 12/1998 | Thomson |
| 5,849,553 | A | 12/1998 | Anderson et al. |
| 5,851,832 | A | 12/1998 | Weiss et al. |
| 5,928,947 | A | 7/1999 | Anderson et al. |
| 5,932,473 | A | 8/1999 | Swiderek et al. |
| 5,958,767 | A | 9/1999 | Snyder et al. |
| 5,981,165 | A | 11/1999 | Weiss et al. |
| 6,040,180 | A | 3/2000 | Johe |
| 6,071,889 | A | 6/2000 | Weiss et al. |
| 6,284,539 | B1 | 9/2001 | Bowen et al. |
| 6,294,346 | B1 | 9/2001 | Weiss et al. |
| 6,399,369 | B1 | 6/2002 | Weiss et al. |
| 6,497,872 | B1 | 12/2002 | Weiss et al. |
| 6,531,464 | B1 | 3/2003 | Szabo et al. |
| 6,699,871 | B2 | 3/2004 | Edmondson et al. |
| 7,101,709 | B2 | 9/2006 | Weiss et al. |
| 7,115,418 | B2 | 10/2006 | Weiss et al. |
| 7,361,505 | B1 | 4/2008 | Weiss et al. |
| 2002/0107273 | A1 | 8/2002 | Nakao et al. |
| 2003/0059369 | A1 | 3/2003 | Kung et al. |

FOREIGN PATENT DOCUMENTS

| | | | |
|---|---|---|---|
| WO | WO 90/06757 | 6/1990 | |
| WO | WO91/02003 | 2/1991 | |
| WO | WO91/09936 | 7/1991 | |
| WO | WO 91/17242 | 11/1991 | |
| WO | WO 93/01275 | 1/1993 | |
| WO | WO 93/09802 | 5/1993 | |
| WO | WO 94/02593 | 2/1994 | |
| WO | WO 94/03199 | 2/1994 | |
| WO | WO 94/04675 | 3/1994 | |
| WO | WO 94/10292 | 5/1994 | |
| WO | WO 95/13364 | 5/1995 | |
| WO | WO 96/09543 | 3/1996 | |
| WO | WO 96/15226 | 5/1996 | |
| WO | WO 98/48001 | 10/1998 | |
| WO | WO 99/01159 | 1/1999 | |
| WO | WO 99/11758 | 3/1999 | |
| WO | WO 00/17323 | 3/2000 | |
| WO | 03000852 | 1/2003 | |
| WO | WO 2006055685 A2 * | 5/2006 | ............ A61K 35/30 |
| WO | 2008002250 | 1/2008 | |

OTHER PUBLICATIONS

Horner PJ, Gage FH. "Regenerating the damaged central nervous system." Nature. Oct. 26, 2000;407(6807):963-70.*

Shihabuddin LS, Horner PJ, Ray J, Gage FH. "Adult spinal cord stem cells generate neurons after transplantation in the adult dentate gyrus." J Neurosci. Dec. 1, 2000;20(23):8727-35.*

Jeong et al., Human Neural Stem Cell Transplantation Promotes Functional Recovery in Rats With Experimental Intracerebral Hemorrhage. Stroke. 2003;34:2258-2263.*

Tarasenko et al., Human Fetal Neural Stem Cells Grafted Into Contusion-Injured Rat Spinal Cords Improve Behavior. Journal of Neuroscience Research 85:47-57 (2007).*

Ahmed, S. et al., "BDNF Enhances the Differentiation but Not the Survival of CNS Stem Cell-Derived Neuronal Precursors," The Journal of Neuroscience, 15(8): 5765-5778 (1995).

Almazan, et al., "Epidermal Growth and Bovine Growth Hormone Stimulate Differentiation and Myelination of Brain Cell Aggregates in Culture", Developmental Brain Research, 21:257-264, (1985).

Almazan, G., et al., "Triiodothyronine Stimulation of Oligodendroglial Differentiation and Myelination", Dev. Neurosci, 7:45-54, (1985).

Anchan, R.M., et al., "EFG and TGF-a Stimulate Retinal Neuroepithelial Cell Proliferation In Vitro", Neuron, 6:923-936, (1991).

Arsenijevic, Y., et al., "Isolation of multipotent neural precursors residing in the cortex of the adult human brain", Experimental Neurology, 170:48-62, (2001).

Avellana-Adalid, V., et al., "Expansion of Rat Oligodendrocyte Progenitors into Proliferative "Oligospheres" that Retain Differentiation Potential", Journal of neuroscience Research, 45:558-570, (1996). http://www3.interscience.wiley.com/cgi-bin/abstract/67559/ABSTRACT.

Baas, P.W. et al., "Polarity orientation of microtubules in hippocampal neurons: Uniformity in the axon and nonuniformity in the dendrite," Proc. Natl. Acad. Sci. USA, vol. 85, pp. 8335-8339 (1988).

Bartlett P. F., "Regulation of Neural Precursor Differentiation in the Embryonic and Adult Forebrain," Clinical and Experimental Pharmacology and Physiology, vol. 22, p. 559-562, 1995.

Bartlett, P.F., et al., "Immortalization of mouse neural precursor cells by the c-myc oncogene", Neurobiology, 85:3255-3259, (1988).

Behl, C., "Apoptosis and Alzheimer's disease", Journal of Neural transmission, 107:1325-1344, (2000).

Bernard, O., et al., "Role of the c-myc and the N-myc Proto-Oncogenes in the Immortalization of Neural Precursors", Journal of Neuroscience Research, 24:9-20, (1989).

Birren, S.J., et al., "A v-myc-Immortalized Sympathoadrenal Progenitor Cell Line in Which Neuronal Differentiation is Initiated by FGF but Not NGF", Neuron, 4:189-201, (1990).

Bjerkvig et al., "Reaggregation of Fetal Rat Brain Cells in a Stationary Culture System I: Methodology and Cell Identification," In Vitro Cellular & Development Biology, 22:4 180-192 (1986).

Bredesen, D.E., et al., "Neural Transplantation Using Temperature-sensitive Immortalized Neural Cells: A Preliminary Report", Annals of Neurology, 27:205-207, (1990).

Bremner, J.D., et al., "Hippocampal volume reduction in major depression" Am. J. Psychiatry, 157:115-117, (2000).

Brezun, J., et al., "Depletion in serotonin decreases neurogenesis in the dentate gyrus and the subventricular zone of adult rats", Neuroscience, 89:999-1002, (1999).

Broe, M., et al., "Relationship between DNA fragmentation, morphological changes and neuronal loss in Alzheimer's disease and dementia with Lewy bodies", Acta Neuropathol, 101:616-624, (2001).

Brüstle O., et al., "Neuronal progenitors as tools for cell replacement in the nervous system," Neurobiology 1996, 6:688-695.

Brüstle O., et al., "Embryonic Stem Cell-Derived Glial Precursors: A Source of Myelinating Transplants", Science, 285:754-756, (1999).

Calof, A.L., et al., "Analysis of neurogenesis in a mammalian neuroepithelium: proliferation and differentiation of an olfactory neuron precursor in vitro", Neuron, 3:115-127, (1989).

Cambray-Deakin, M.A., "The expression of excitatory amino acid binding sites during neuritogenesis in the developing rat cerebellum", Biol Abstr, 90:78577, (1990).

Cameron, H.A., et al., "Regulation of neurogenesis by growth factors and neurotransmitters", Journal of Neurobiology, 36:287-306, (1998).

Cao, Q., et al., "Stem Cell Repair of Central Nervous System Injury", Journal of Neuroscience Research, 68:501-510, (2002).

Carpenter, M.K., et al., "Generation and Transplantation of EGF-Responsive Neural Stem Cells Derived from GFAP-hNGF Transgenic Mice", Experimental Neurology, 148:187-204, (1997).

Carpenter, M.K., et al., "In Vitro Expansion of a Multipotent Population of Human Neural Progenitor Cells", Experimental Neurology, 158:265-278, (1999).

Carpenter reexamination application No. 90/008,862 (reexamination of U.S. Pat. No. 6,103,530) entitled "Cultures of Human CNS Neural Stem Cells," filed Oct. 2, 2007.

Castillo, S.O., et al., "Dopamine Biosynthesis is Selectively Abolished in Substantia Nigra/Ventral Tegmental Area but Not in Hypo- (56) References Cited

OTHER PUBLICATIONS thalamic Neurons in Mice with Targeted Disruption of the Nurr1 Gene", Molecular and Cellular Neuroscience, 11:36-46, (1998).
Castillo, S.O., et al., "Organization, Sequence, Chromosomal Localization, and Promoter Identification of the Mouse Orphan Nuclear Receptor Nurr1 Gene", Genomics, 41:250-257, (1997).
Cattaneo, E., et al., "Proliferation and differentiation of neuronal stem cells regulated by nerve growth factor", Letters to Nature, 347:762-765, (1990).
Cepko, C.L., "Immortalization of Neural Cells Via Retrovirus-Mediated Oncogene Transduction", Annu. Rev. Neurosci., 12:47-65, (1989).
Chabot, P., "Transient expression of an intermediate filament-associated protein (IFAPa-400) during in vivo and in vitro differentiation of chick embryonic cells derived form neuroectoderm", Biol Abstr, 90:78578, (1990).
Conover, J.C. et al., "Ciliary neurotrophic factor maintains the pluripotentiality of embryonic stem cells," Development 119, 559-565 (1993).
Coon, H.G., et al., "Cell cultures of neuroblasts from rat olfactory epithelium that show odorant responses", Neurobiology, 86:1703-1707, (1989).
Coppell, A.L., et al., "Bi-phasic change in BDNF gene expression following antidepressant drug treatment", Neuropharmcaology, 44:903-910, (2003).
Cummings, B.J., et al., "Human Neural Stem Cells Differentiate and Promote Locomotor Recovery in Spinal Cord-Injured Mice", Proceedings of the National Academy of Sciences of the United States of America, 102(39):14069-14074, (2005).
Czeh, B., et al., "Stress-induced changes in cerebral metabolites, hippocampal volume, and cell proliferation are prevented by antidepressant treatment with tianepine", PNAS, 98:12796-12801, (2001).
Dahlstrand et al., "Nestin mRNA expression correlates with the central nervous system progenitor cell state in many, but not all, regions of developing central nervous system," Developmental Brain Research 84:109-129 (1995).
Davis, A., et al., "A self-renewing multipotential stem cell in embryonic rat cerebral cortex", Letters to Nature, 372:263-266, (1994).
DiCicco-Bloom, E., et al., "Neuroblast Mitosis in Dissociated Culture: Regulation and Relationship to Differentiation", The Journal of Cell Biology, 110:2073-2086, (1990).
Doering et al., "Isolation and identification of neuroblast precursor cells from mouse neopallium," Developmental Brain Research 5:229-233 (1982).
Drago, J., et al., "A Method for the Isolation of Purified Murine Neuroepithelial Cells from the Developing Mouse Brain", Journal of Neuroscience Methods, 37:251-256, (1991).
Drago, J., et al., "Basic Fibroblast Growth Factor Upregulates Steady-State Levels of Laminin B1 and B2 Chain mRNA in Cultured Neuroepithelial Cells", Experimental Cell Research, 196:246-254, (1991).
Drago, J., et al., "Fibroblast Growth Factor-Mediated Proliferation of Central Nervous System Precursors Depends on Endogenous Production of Insulin-like Growth Factor I", Neurobiology, 88:2199-2203, (1991).
Drago, J., et al., "Laminin through its Long Arm E8 Fragment Promotes the Proliferation and Differentiation of Murine Neuroepithelial Cells in Vitro", Experimental Cell Research, 192:256-265, (1991).
D'Sa, C. et al., "Antidepressants and neuroplasticity", Bipolar Disorders, 4:183-194, (2002).
Dutton, G.R., "Isolation, Culture, and Use of Viable Central nervous System Perikarya", Methods in Neuroscience, 2:87-102, (1990).
Eccleston et al., "Requirements for Brain Cell Attachment, Survival and Growth in Serum-Free Medium: Effects of Extracellular Matrix, Epidermal Growth Factor and Fibroblast Growth Factor" Dev. Neurosci 7:308-322 (1985).

Ehrlich, M.E., et al., "DARPP-32 development in the caudate nucleus is independent of afferent input from the substantia nigra", Biol. Abstr. vol. 90(78582), (1990).
Eilers, M., et al., "Chimaeras of Myc oncoprotein and steroid receptors cause hormone-dependent transformation of cells", Letters to Nature, 340:66-68, (1989).
Engebraaten et al., "Effects of EGF, bFGF, NGF and PDGF(bb) on cell proliferative, migratory and invasive capacities of human brain-tumor biopsies in vitro," Int. J. Cancer, 53:209-214 (1993).
Eriksson, P.S., et al., "Neurogenesis in the adult human hippocampus", Nature Medicine, 4:1313-1317, (1998).
Escary, J. et al., "Leukaemia inhibitory factor is necessary for maintenance of haematopoietic stem cells and thymocyte stimulation," Nature, vol. 363, pp. 361-364 (1993).
Evans, R.M., "The Steroid and Thyroid Hormone Receptor Superfamily," Science, vol. 240, pp. 889-895 (1988).
Evrard, C. et al., "Immortalization of bipotential and plastic glio-neuronal precursor cells," Proc. Natl. Acad. Sci. USA, vol. 87, pp. 3062-3066 (1990).
Falk, A., et al., "Amphiregulin is a mitogen for adult neural stem cells", Journal of Neuroscience Research, 69:757-762, (2002).
Feldman, D.H., et al., "Differentiation of Ionic Currents in CNS Progenitor Cells: Dependence upon Substrate Attachment and Epidermal Growth Factor," Experimental Neurology 140, 206-217 (1996).
Feron, F., et al., "Stress induces neurogenesis in non-neuronal cell cultures of adult olfactory epithelium", Neuroscience, 88:571-583, (1999).
Finger, S., et al., "Nimodipine and Neural Grafts", Duke Med. Cent. Lib., 34(1'2):208, (1991).
Finley, M. et al., "Synapse Formation and Establishment of Neuronal Polarity by P19 Embryonic Carcinoma and Embryonic Stem Cells," The Journal of Neurosciences, 16(3): 1056-1065 (1996).
Fischer, A.J., et al., "Exogenous Growth Factors Induce the Production of Ganglion Cells at the Retinal Margin", Development, 129:2283-2291, (2002).
Flax J.D., et al., "Engraftable human neural stem cells respond to developmental cues, replace neurons, and express foreign genes", Nature Biotechnology, 16:1033-1039, (1998).
Frappaz, D., et al., "Enhancement of Growth of Primary Metastatic Fresh Human Tumors of the Nervous system by Epidermal Growth Factor in Serum-free Short Term Culture", Neurosurgery, 23:355-359, (1988).
Frederiksen, K. et al., "Immortalization of Precursor Cells from the Mammalian CNS," Neuron, vol. 1, 439-448 (1988).
Fujiwara, Y., et al., "Intravenously Injected Neural Progenitor Cells of Transgenic Rats Can Migrate to the Injured Spinal Cord and Differentiate into Neurons, Astrocytes and Oligodendrocytes", Neuroscience Letters, 366(3):287-291, (2004).
Gage, F.H. et al., "Survival and differentiation of adult neuronal progenitor cells transplanted to the adult brain," Proc. Natl. Acad. Sci., vol. 92, pp. 11879-11883, Dec. 1995.
Glasky, et al., "Update: Central and Peripheral Nervous Systems AIT-082, a novel purine derivative with neuroregenerative properties", Exp. Opin. Invest. Drugs, 6:1413-1417, (1997).
Godfraind, C. et al., "In Vivo Analysis of Glial Cell Phenotypes during a Viral Demyelinating Disease in Mice," The Journal of Cell Biology, vol. 109, pp. 2405-2416 (1989).
Goldman, S.A., et al., "In vitro neurogenesis by neuronal precursor cells derived from the adult songbird brain", The Journal of Neuroscience, 12:2532-2541, (1992).
Gould, E., et al., "Inaugural Article: Adult-generated hippocampal and neocortical neurons in macaques have a transient existence", PNAS, 98:10910-10917, (2001).
Green, S., et al., "Human oestrogen receptor cDNA: sequence, expression and homology to v-erb-A", Nature, 320:134-139, (1986).
Gritti, A., et al., "Multipotential Stem Cells from the Adult Mouse Brain Proliferate and Self-Renew in Response to Basic Fibroblast Growth Factor", The Journal of Neuroscience, 16:1091-1100, (1996).

(56) References Cited

OTHER PUBLICATIONS

Gu W. et al., "Cortical neurogenesis in adult rats after reversible photothrombotic stroke", Journal of Cerebral Blood Flow and Metabolism, vol. 20, pp. 1166-1173, 2000.
Guentert-Lauber, B. et al., "Responsiveness of Astrocytes in Serum-Free AggregateCultures to Epidermal Growth Factor: Dependence on the Cell Cycle and the Epidermal Growth Factor Concentration," Dev. Neurosci. 7: 286-295 (1985).
Hall, et al., "An Introduction to Molecular Neurobiology", p. 357, 1992.
Hata, M., et al., "A decrease in the wet-dog shakes response to the second administration of kainic acid in juvenile rats", Biol. Abstr., 92(31831), (1991).
Hauser, K.F., et al., "Opioids intrinsically inhibit the genesis of mouse cerebellar granule neuron precursors in vitro: differential impact of mu and delta receptor activation on proliferation and neurite elongation", European Journal of Neuroscience, 12:1291-1293, (2000).
Hermanson, M., et al., "PDGF and its receptors following facial nerve axotomy in rats: expression in neurons and surrounding glia", Exp. Brain Res., 102:415-422, (1995).
Hockfield et al., "Identification of Major Cell Classes in the Developing Mammalian Nervous System," The Journal of Neuroscience 5:12 3310-3328 (1985).
Hollenberg et al., "Epidermal Growth Factor: Receptors in Human Fibroblasts and Modulation of Action by Cholera Toxin," Proc. Nat. Acad. Sci. USA, vol. 70, No. 10, pp. 2964-2968, Oct. 1973.
Honegger, P., et al., "Growth and Differentiation of Aggregating Fetal Brain Cells in a Serum-Free Defined Medium", Nature, 282:305-308, (1979).
Honkaniemi, J., et al., "Focal brain injury induces multiple immediate early genes encoding zinc finger transcription factors", Molecular Brain Research, 28:157-163, (1995).
Horcholle-Bossavit, G., et al., "Postnatal development of peroneal motoneurons in the kitten", Biol. Abstr., (78579), (1990).
Hoshimaru, M., et al., "Differentiation of the immortalized adult neuronal progenitor ce line HC2S2 into neurons by regulatable suppresision of the v-myc oncogene", Proc. Natl. Acad., 93:1518-1523, (1996).
Howland, et al., "Focal loss of the glutamate transporter EAAT2 in a transgenic rat model of SOD1 mutant-mediated amyotrophic lateral sclerosis (ALS)", PNAS, 99:1604-1609, (2002).
Hunter, S.F., et al., "Growth factor responses of enriched bipotential glial progenitors", Biol. Abstr., 90(78577), (1990).
Isacson, O., "The production and use of cells as therapeutic agents in neurodegenerative diseases," The Lancet Neurology, 2:417-424, (2003).
Ishibashi, et al., "Human Neural Stem/Progenitor Cells, Expanded in Long-Term Neurosphere Culture, Promote Functional Recovery After Focal Ischemia in Mongolian Gerbils", Journal of Neuroscience Research, 78:215-223, (2004).
Jain, M., et al., "GABAergic Immunoreactivity is Predominant in Neurons Dervied From Expanded Human Neural Precursor Cells In Vitro", Experimental Neurology, 182(1):113-123, (2003).
Jelitai, M., et al., "Regulated appearance of NMDA Receptor Subunits and Channel Functions Duriing in Vitro Neuronal Differentiation", Journal of Neurobiology, 51:54-65, (2002).
Jin, K., et al., "Stem cell factor stimulates neurogenesis in vitro and in vivo", The Journal of Clinical Investigation, 110:311-319, (2002).
Jin, K., et al., "Vascular endothelial growth factor (VEGF) stimulates neurogenesis in vitro and in vivo", PNAS, 99:11946-11950, (2002).
Johe, K. et al., "Single factors direct the differentiation of stem cells from the fetal and adult central nervous system," Genes & Development, vol. 10, pp. 3129-3140, 1996.
Jones-Villeneuve, et al., "Retinoic Acid Induces Embryonal Carcinoma Cells to Differentiate into Neurons and Glial Cells", The Journal of Cell Biology, 94:253-262, (1982).
Jung, et al., "Novel pluripotential neural progenitor lines exhibiting rapid controlled differentiation to neurotransmitter receptor-expressing neurons and glia," Eur. J. Neuroscj., vol. 10 pp. 3246-3256 (1998).
Kehl, L.J., et al., "Neurogenesis in postnatal rat spinal cord: a study in primary culture", Science, 276:586-589, (1997).
Kempermann, G., et al., "Depressed new neurons-adult hippocampal neurogenesis and a cellular plasticity hypothesis of major depression", Biological Psychiatry, 54:499-503, (2003).
Kempermann, G., et al., "Genetic determinants of adult hippocampal neurogenesis correlate with acquisition, but not probe trial performance, in the water maze task", European Journal of Neuroscience, 16:129-136, (2002).
Kershaw, T.R., et al., "Foetal H-2Kb-tsA58 Transgenic Mouse Tissue Develops in a Similar Manner to ISO Geneic Foetal Tissue when Transplanted into Adult Mouse Brain", Duke Med. Cent. Lib., 34(4):208, (1991).
Kilpatrick, et al., "Cloning and Growth of Multipotential Neural Precursors: Requirements for Proliferation and Differentiation", Neuron, 10:255-265, (1993).
Kilpatrick, T.J., Richards, L.J., and Bartlett, P.F., "The Regulation of Neural Precursor Cells within the Mammalian Brain," Mol. Cell. Neurosci., 6, 2-15, (1995).
Kilpatrick, T.J., and Bartlett, P.F., "Cloned Multipotential Precursors from the Mouse Cerebrum Require FGF-2, Whereas Glial Restricted Precursors are Stimulated with Either FGF-2 or EGF," J. Neurosci., 15(5):3653-3661 (1995).
Kitani, H., et al., "Isolation and Characterization of Mouse Neural Precursor Cells in Primary Culture", In Vitro Cell. Dev. Biol., 27A:615-624, (1991).
Kuhn, H.G., et al., "Neurogenesis in the dentate gyrus of the adult rat: age-related decrease of neuronal progeneitor proliferation", The Journal of Neuroscience, 16:2027-2033, (1996).
Kumar, et al., "Localisation of the oestradiol-binding and putative DNA-binding domains of the human oestrogen receptor," The EMBO Journal, vol. 5, No. 9, pp. 2231-2236, (1986).
Law et al., "Identification of New Brain-Specific Transcription Factor, NURR 1," Molecular Endocrinology, pp. 2129-2135, 1992.
Law, et al., "Molecular Cloning of a Novel Member of theNuclear Receptor Superfamily Realted to the Orphan Receptor, TR2," Gene Expr., vol. 4, pp. 77-84, (1994).
Lee, et al., The v-myconcogene, Oncogene, 18:2997-3003, (1999).
Lee, A.L., et al., "Stress and depression: possible links to neurons death in the hippocampus", Bipolar Disorders, 4:117-128, (2002).
Lee, J., et al., "Dietary restriction increases the number of newly generated neural cells, and induces BDNF expression, in the dentate gyrus of rats", Journal of Molecular Neuroscience, 15:99-108, (2001).
Lendahl et al., "CNS Stem Cells Express a New Class of Intermediate Filament Protein," Cell 60:585-595 (1990).
Lepore, A.C., et al., "Neural Precursor Cells Can be Delivered into the Injured Cervical Spinal Cord by Intrathecal Injection at the Lumbar Cord", Brain Research, 1045(1-2):206-216, (2005).
Lichtenwalner, R.J., et al., "Intracerebroventricular infusion of insulin-like growth factor-I ameliorates the age-related decline in hippocampal neurogenesis", Neuroscience, 107:603-613, (2001).
Lindvall, et al., "Stem cell therapy for human neurodegenerative disorders—how to make it work," Nature Med., 10:S42-S50, (2004).
Ling, et al., "Differentiation of Mesencephalic Progenitor Cells into Dopaminergic Neurons by Cytokines," Exp. Neurol., 149, 411-423, (1998).
Littlewood, T.D., et al., "A modified oestrogen receeptor liganbinding domain as an improved switch for the regulation of heterologous proteins". Nucleic Acids Research. 1995, vol. 23, No. 10, pp. 1686-1690, see abstract.
Llado, J. et al., "Neural Stem Cells Protect Againist Glutamate-Induced Excitotoxicity and Promote Survival of Injured Motor Neurons Thrrough the Secretion of Neurotrophic Factors," Molecular and Cellular Neurosciences, 27(3):322-331, (2004).
Lois, et al., "Proliferating subventricular zone cells in the adult mammalian forebrain can differentiate into neurons and glia," Proc. Nat'l Acad. Sci., 90:2074-2077, (1993).

(56) References Cited

OTHER PUBLICATIONS

Lovejoy, D.A., et al., "Primary structure of two forms of gonadotropin-releasing hormone from brains of the American alligator", Biol. Abstr., 92(31827), (1991).
Lucassen, P.J., et al., "Hippocampal apoptosis in major depression is a minor event and absent from subareas at risk for glucocorticoid overexposure", American Journal of Pathology, 158:453-468, (2001).
Lumsden, A. et al., "Patterning the Vertibrate Neuraxis," Science, vol. 274, pp. 1109-1115, Nov. 15, 1996.
Lyman, W.D., et al., "Human Fetal Central Nervous System Organotypic Cultures", Developmental Brain Research, 60:155-160, (1991).
Ma, W., et al., "Acetylcholine stimulates cortical precursor cell proliferation in vitro via muscarinic receptor activation and MAP kinase phosphorylation", European Journal of Neuroscience, 12:1227-1240, (2000).
Madsen, T.M., et al., "Increased neurogenesis in a model of electroconvulsive therapy", Biological Psychiatry, 47:1043-1049, (2000).
Mages, H. et al., "NOT, A Human Immediate-Early Response Gene Closely Related to the Steroid/Thyroid Hormone Receptor NAK1/TR3," Molecular Endocrinology, p. 1583-1591, 1994.
Malberg, J.E., et al., "Chronic antidepressant treatment increases neurogenesis in adult rat hippocampus", The Journal of Neuroscience, 20:9104-9110, (2000).
Marin, N., et al., "0.-amyloid-induced activation of caspase-3 in primary cultures of rat neurons", Mechanisms of Ageing and Development, 119:63-67, (2000).
Marsala, M., et al., "Spinal Implantation of hNT Neurons and Neuronal Precursors: Graft Survival and Functional Effects in Rats with Ischemic Spastic Paraplegia", European Journal of Neuroscience, 20(9):2401-2414, (2004).
Martz et al., "The Role of Cell-cell Contact in "Contact" Inhibition of Cell Division: A Review and New Evidence," J. Cell. Physiol., 79:189-210, (1971).
Masters, B.A., "Insulin-like growth factor I (IFG-I) receptors and IGF-I action in oligodendrocytes from rat brains", Biol. Abstr., 92(31828), (1991).
Mattson, M.P., "Stem cells as therapeutics for neurodegenerative disorders?" Expert Rev. Neurotherapeutics, 267-273, (2001).
Mauerhoff, T. et al., "Differential Expression and Regulation of Major Histocompatibility Complex (MHC) Products in Neural and Glial Cells of the Human Fetal Brain", Journal of Neuroimmunology, 18:271-289, (1988).
Mayo, W., et al., "Pregnenolone sulfate and aging of cognitive functions: behavioral, neurochemical, and morphological investigations", Hormones and Behavior, 40:215-217, (2001).
McCarthy, M., et al., "Infection of Human Neural Cell Aggregate Cultures with a Clinical Isolate of Cytomegalovirus", Journal of Neuropathology and Experimental Neurology, 50:441-450, (1991).
McConnell, S., "Constructing the Cerebral Cortex: Neurogenesis and Fate Determination," Neuron, vol. 15, 761-768, Oct. 1995.
McKay, R., et al., "Mechanisms Regulating Cell number and Type in the Mammalian Central Nervous System", Cold Spring Harbor Symposia on Quantitative Biology, LV:291-301, (1990).
McKay, R., et al., "Stem Cells in the Developing and Adult Brain," (abs.) (1995).
McKay, R., et al., "Stem Cells in the Central Nervous System," Science, 276, pp. 66-71 (1997).
Mervaala, E., et al., "Quantitative MRI of the hippocampus and amygdala in severe depression", Psychological Medicine, 30:117-125, (2000).
Monnet-Tschudi, F. et al. "Influence of Epidermal Growth Factor on the Maturation of Fetal Rat Brain Cells in Aggregate Culture," Dev Neurosci 1989, vol. 11, pp. 30-40.
Morrison, R.S., et al., "Trophic Stimulation of Cultured Neurons from Neonatal Rat Brain by Epidermal Growth Factor", Science, 238:72-75, (1987).

Morrison, S.J., et al., "Regulatory Mechanisms in Stem Cell Biology," Cell, vol. 88,287-298, Feb. 7, 1997.
Morshead et al., "Postmitotic Death is the Fate of Constitutively Proliferating Cells in the Subependymal Layer of the Adult Mouse Brain," The Journal of Neuroscience 12(1):249-256 (1992).
Morshead et al., "Neural Stem Cells in the Adult Mammalian Forebrain: A Relatively Quiescent Subpopulation of Subependymal Cells," Neuron 13:1071-1082 (1994).
Murphy, M., et al., "Fibroblast Growth Factor Stimulates the Proliferation and Differentiation of Neural Precursor Cells In Vitro", Journal of Neuroscience Research, 25:463-475, (1990).
Murrell, W., et al., "Neurogenesis in adult human", NeuroReport, 7:1189-1194, (1996).
Mytilineou, C., et al., "Epidermal Growth Factor-Induced Survival and Proliferation of Neuronal Precursor Cells from Embryonic Rat Mesencephalon", Neuroscience Letters, 135:62-66, (1992).
Nakafuku, et al., "Establishment and Characterization of a Multipotential Neural Cell Line that can Conditionally Generate Neurons, Astrocytes, and Oligodendrocytes In Vitro", Journal of Neuroscience Research, 41:153-168, (1995).
Nakagawa, S., et al., "Regulation of neurogenesis in adult mouse hippocampus by cAMP and the cAMP reponse element-binding protein", The Journal of Neuroscience, 22:3673-3682, (2002).
Nestler, E.J., et al., "Neurobiology of Depression", Neuron, 34:13-25, (2002).
Nibuya, M., et al., "Chronic antidepressant administration increases the expression of cAMP response element binding protein (CREB) in rat hippocampus", The Journal of Neuroscience, 16:2365-2372, (1996).
Nielsen, F.C., et al., "Receptor Binding, Endocytosis, and Mitogenesis of Insulin-Like Growth Factors I and II in Fetal Rat Brain Neurons", Journal of Neurochemistry, 56:12-21, (1991).
Nolte, J., "Introduction to the Nervous System," The Human Brain an Introduction to its Functional Anatomy, Fourth Edition pp. 1-35 (1999).
Ohkura, et al., "Structure, mapping and expression of a human NOR-1 gene, the third member of the Nur77/NGFI-B family," Biochim. Biophys. Acta, 1308:205-214, (1996).
Oka, S., et al, "Autologous Transplantation of Expanded Neural Precursor Cells Into the Demyelinated Monkey Spinal Cord", Brain Research, 1030(1):94-102, (2004).
Okabe, et al., "cDNA Cloning of a NGFI-B/nur77-Related Transcription Factor from an Apoptotic Human T Cell Line," J. Immunol., 154:3871-3879, (1995).
Okano, et al., "Neural stem cells and regeneration of injured spinal cord", Kidney International, 68:1927-1931, (2005).
Okano, H., "Neural stem cells: progression of basic research and perspective for clinical application," Keio Journal of Medicine, vol. 51, pp. 115-128, 2002.
Palmer T D. et al., "The Adult Rat Hippocampus Contains Primordial Neural Stem Cells," Molecular and Cellular Neuroscience 8, 389-404 (1997).
Palmer T D. et al., "Fibroblast growth factor-2 activates a latent neurogenic program in neural stem cells from diverse regions of the adult CNS," The Journal of Neuroscience, vol. 19, pp. 8487-8497, 1999.
Park K. et al., "Global gene and cell replacement strategies via stem cells," Gene Therapy, vol. 9, pp. 613-624, 2002.
Pena de Ortiz et al., "HZF-3, an immediate-early orphan receptor homologous to NURR1/NOT: Induction upon membrane depolarization and seizures," Mol. Brain Res. 38:1-13 (1996).
Perrone-Capano et al., "Epigenetic factors and midbrain dopaminergic neurone development," Bioessays vol. 18 No. 10 pp. 817-824 (1996).
Peterson D. A. et al., "Trophic factor therapy for neuronal death," Alzheimer Disease, 2nd Edition, Chapter 25, pp. 373-388, 1999.
Pham, K. et al., "Repeated restraint stress suppresses neurogenesis and induces biphasic PSA-NCAM expression in the adult dentate gyrus," European Journal of Neuroscience, vol. 17, pp. 879-886, 2003.
Piescinski, P. et al., "Neurogenesis of the amygdaloid complex in the rhesus monkey," Society for Neuroscience Abstracts, vol. 16, p. 1147, 1990.

(56) References Cited

OTHER PUBLICATIONS

Pincus D W. et al., "In vitro neurogenesis by adult human epileptic temporal neocortex," Clinical Neurosurgery, Chapter 2, pp. 17-25.
Pollerberg et al., "Generation of Cell Lines From Embryonic Quail Retina Capable of Mature Neuronal Differentiation," Journal of Neuroscience Research, vol. 41, pp. 427-442, 1995.
Price, "Brain Stems," Current Biology 5:3 232-234 (1995).
Pucilowski, 0. et al., "Decreased hyperthermic effect of MK801 in selectively bred hypercholinergic rats," Ref. No. 31825, Biol Abstr vol. 92, 1991.
Pulliam, L. et al., "A Normal Human Brain Cell Aggregate Model for Neurobiological Studies," Journal of Neuroscience Research, vol. 21, pp. 521-230, 1988.
Qian, X et al., "FGF2 Concentration Regulates the Generation of Neurons and Glia from Multipotent Cortical Stem Cells," Neuron, vol. 18, pp. 81-93, Jan. 1997.
Qu, T. et al., "Human neural stem cells improve cognitive function of aged brain," NeuroReport, vol. 12, pp. 1127-1132, 2001.
Raina, A K. et al., "Abortive apoptosis in Alzheimer's disease," Acta Neuropathol, vol. 101, pp. 305-310, 2001.
Rajan et al., "Neural Stem Cells and Their Munipulation," (2006) Methods in Ezymol. 419:23-52.
Rakic, P. "Radial Versus Tangential Migration of Neuronal Clones in the Developing Cerebral Cortex," Proc. Natl. Acad. Sci, USA, vol. 92, pp. 11323-11327, Dec. 1995.
Rao et al., "Immortalization and Controlled In Vitro Differentiation of Murine Multipotent Neural Crest Stem Cells," (1997) J. Neurobiol. 32, 722.
Rathbone M P. et al., "Trophic effects of purines in neurons and glial cells," Progress in Neurobiology, vol. 59, pp. 663-690, 1999.
Ray, J. and Gage, F.H., "Spinal Cord Neuroblasts Proliferate in Response to Basic Fibroblast Growth Factor," J. Neurosci. 14(6): 3548-3564 (1994).
Ray, J. Peterson, D., Schinstine, M. & Gage, F., "Proliferation, differentiation, and long-term culture of primary hippocampal neurons," Proc. Natl. Acad. Sci. USA vol. 90, pp. 3602-3606 (1993).
Redies et al., "Differentiation and Heterogeneity in T-Antigen Immortalized Precursor Cell Lines from Mouse Cerebellum," Journal of Neuroscience Research 30:601-615 (1991).
Reichmann et al., "Activation of an Inducible c-FosER Fusion Protein Causes Loss of Epithelial Polarity and Triggers Epithelial-Fibroblastoid Cell Conversion," (1992) Cell vol. 71, pp. 1103-1116.
Renoncourt et al., Neurons derived in vitro from ES cells express homeoproteins characteristic of motoneurons and interneurons (1998) Mechanisms of Development 79 pp. 185-197.
Resnick, J et al., "Long-term proliferation of mouse primordial germ cells in culture," Nature, vol. 359, pp. 550-551, Oct. 8, 1992.
Rettig, W.J. et al., "Cell Type-specific Control of Human Neuronectin Secretion by Polypeptide mediators and Phorbol Ester," The Journal of Histochemistry and Cytochemistry, vol. 37, pp. 1777-1786, 1989.
Rettig, W.J. et al., "Stimulation of Human Neuronectin Secretion by Brain-Derived Growth Factors," Brain Research, vol. 487, pp. 171-177, 1989.
Reynolds, B.A. et al., "A Multipotent EFG-Responsive Striatal Embryonic Progenitor Cell Produces Neuron and Astrocytes," The Journal of Neuroscience, vol. 12, pp. 4565-4574, 1992.
Reynolds, B.A. et al., "A Non-Transformed, Growth Factor Dependent Stem Cell Line Derived from the Embryonic Mouse CNS Produces Neurons, Astrocytes and Oligodendrocytes," Duke Med Cent Lib 34.P3, p. 208, 1991.
Reynolds, B.A. et al., "EGF- and TGFα-responsive striatal embryonic progenitor cells produce both neurons and astrocytes," Society for Neuroscience Abstracts, vol. 16, p. 1147, 1990.
Reynolds, B.A. et al., "Generation of Neurons and Astocytes from Isolated Cells of the Adult Mammalian Central Nervous System," Science, vol. 255, pp. 1707-1709, 1992.
Reynolds, B.A. et al., "Clonal and Population Analyses Demonstrate That an EGF-Responsive Mammalian Embryonic CNS Precursor is a Stem Cell," Developmental Biology 175, 1-13 (1996).

Righi et al., myc-Immortalized Microglial Cells Express a Functional Platelet-Activating Factor Receptor (1995) J. Neurochem. 64, 121-129.
Rind H. et al., "Synaptic Targeting of Retrogradely Transported Trophic Factors in Mononeurons: Comparison of Glial Cell Line-Derived Neurotrophic Factor, Brain-Derived Neurotrophic Factor, and Cardiotrophin-1 with Tetanus Toxin," The Journal of Neuroscience, vol. 25, pp. 539-549, 2005.
Romand, R. et al., "Development of tonotopy oin the inferior colliculus: 1. Electrophysiological mapping in house mice," Ref. No. 78577. Biol Abstr vol. 90, 1990, 78580.
Roth, K. A., "Caspases, apoptosis, and Alzheimer disease: causation, correlation, and confusion," Journal of Neuropathology and Experimental Neurology, vol. 60, pp. 829-838, 2001.
Rothstein J.D. et al., "Decreased Glutamate Transport by the Brain and Spinal Cord in Amyotrophic Lateral Sclerosis," The New England Journal of Medicine, vol. 326, pp. 1464-1468, 1992.
Roy N. S, et al., "In vitro neurogenesis by progenitor cells isolated from the adult human hippocampus," Nature Medicine, vol. 6, pp. 271-277, 2000.
Rozental R. et al., "Differentiation of hippocampal progenitor cells in vitro: temporal expression of intercellular coupling and voltage- and ligand-gated responses," Developmental Biology, vol. 167, pp. 350-362, 1995.
Rudland, P.S. et al., "Growth Control in cultured Mouse Fibroblasts: Induction of the Pleiotypic and Mitogenic Responses by a Purified Growth Factor," Proc. Nat. Acad. Sci., vol. 71, No. 7, pp. 2600-2604, Jul. 1974.
Rutka, J.T. et al., "Characterization of Fetal Human Brain Cultures," Dev. Neurosci., vol. 9, pp. 154-173, 1987.
Ryder et al., "Establishment and Characterization of Multipotent Neural Cell Lines Using Retrovirus Vector-Mediated Oncogene Transfer," (1990) J. Neurobiol vol. 21, No. 2, pp. 356-375.
Sabate, O., Horellou, P., Vigne, E., Colin, P., Perricaudet, M., Buc-Caron, M.-H. & Mallet, J., "Transplantation to the rat brain of human neural progenitors that were genetically modified using adenoviruses," Nature Genetics 9, 256-260 (1995).
Sah et al., "Bipotent progenitor cell lines from the human CNS," (1997) Nature Biotech. 15:574.
Sales, N. et al., Neutral endopeptidase 24.11 in rat peripheral tissues: comparative localization bby "ex vivo" and "in vitroautoradiography," Ref. No. 31832, Biol Abstr vol. 92, 1991, 31829.
Saneto, R.P. et al., "Insulin/Insulin-Like Growth Factor I and Other Epigenetic Modulators of Myelin Basic Protein Expression in Isolated Oligodendrocyte Progenitor Cells," Journal of Neuroscience Research, Vo. 21, pp. 210-219, 1988.
Santarelli, L. et al., "Requirement of hippocampal neurogenesis for the behavioral effects of antidepressants," Science, vol. 301, pp. 805-809, 2003.
Sato, H. et al., "Somatostatin receptors in the senescent rat brain: A quantitative autoradiographic study," Ref. No. 31826, Biol Abstr vol. 92, 1991.
Satoh M. et al., "Promotion of neurogenesis in mouse olfactory neuronal progenitor cells by leukemia inhibitory factor in vitro," Neuroscience Letters, vol. 225, pp. 165-168, 1997.
Saucedo-Cardenas et al., "Cloning and structural organization of the gene encoding the murine nuclear receptor transcription factor, NURR1," Gene 187:135-139 (1997).
Saucedo-Cardenas et al., "Nurr1 is essential for the induction of the dopaminergic phenotype and the survival of ventral mesencephalic late dopaminergic precursor neurons," Proc. Natl. Acad. Sci. USA 95:4013-4018 (1998).
Scearce et al., "RNR-1, a Nuclear Receptor in the NGFI-B/Nur77 Family that is Rapidly Induced in Regenerating Liver," J. Biol. Chem. vol. 268, No. 12, pp. 8855-8861 (1993).
Schapira, A., "Pathogenesis of Parkinson's disease," Bailliere's Clin. Neurol. vol. 6, No. 1, pp. 15-36 (1997).
Schinstine, M. et al., "Expression of Neuronal Antigens by Astrocytes Derived from EGF-Generated Neuroprogenitor Cells," Experimental Neurology 141, 67-78 (1996).

(56) References Cited

OTHER PUBLICATIONS

Schlaggar, B.L. et al., "Potential of Visual Cortex to Develop an Array of Functional Units Unique to Somatosensory Cortex," Science, vol. 252, pp. 1556-1560 (1991).
Scott B W. et al., "Neurogenesis in the dentate gyrus of the rat following electroconvulsive shock seizures," Experimental Neurology, vol. 165, pp. 231-236, 2000.
Seaberg R M. et al., "Adult rodent neurogenic regions: the ventricular subependyma contains neural stem cells, but the dentate gyrus contains restricted progenitors," The Journal of Neuroscience, vol. 22, pp. 1784-1793, 2002.
Seigel, G.M. et al., "Differentiation of oncogenically altered chick neuroretinal cells by succinylated concanavalin A," Society for Neuroscience Abstracts, vol. 16, p. 1147, 1990.
Selvakumarun et al., "Myeloblastic Leukemia Cells Conditionally Blocked by Myc-Estrogen Receptor Chimeric transgenes for Terminal Differentiation Coupled to Growth Arrest and Apoptosis," (1993) Blood vol. 81, No. 9, pp. 2257-2262.
Shingo T. et al., "Erythropoietin regulates the in vitro and in vivo production of neuronal progenitors by mammalian forebrain neural stem cells," The Journal of Neuroscience, vol. 21, pp. 9733-9743, 2001.
Shirayama, Y. et al., "Brain-derived neurotrophic factor produces antidepressant effects in behavioral models of depression," The Journal of Neuroscience, vol. 22, pp. 3251-3261, 2002.
Shors T J. et al., "Neurogenesis in the adult is involved in the formation of trace memories," Nature, vol. 410, pp. 372-376, 2001.
Shou J. et al., "BMPs inhibit neurogenesis by a mechanism involving degradation of a transcription factor," Nature Neuroscience, vol. 2, pp. 339-345, 1999.
Sigma-Aldrich, Material Safety Data Sheet for Ethylenediaminetetraacetic Acid, for Complexometry, pp. 1-7 (1995).
Silani, V. et al., "Human Neuronal Cells in Culture: From Concepts to Basic Methodology," Boll. 1st. Sieroter. Mila., vol. 69, pp. 309-313, 1990.
Snyder et al., "Taking Stock and Planning for the Next Decade: Realistic Prospects for Stem Cell Therapies for the Nervous System," (2004) J. Neurosci. Res. 76:157-168.
Sorensen, K.A. et al., "Postembryonic neurogenesis in the Brain of Manduca Sexta," Society for Neuroscience Abstracts, vol. 16, p. 1147, 1990.
Stemple, D. et al., "Neural Stem Cells are Blasting Off," Neuron, vol. 18, 1-4, Jan. 1997.
Sternfeld, M.D. et al., "Cultured Human Retinal Pigment Epithelial Cells Express Basic Fibroblast Growth Factor and its Receptor," Current Eye Research, vol. 8, pp. 1029-1037, 1989.
Stewart, J.S. et al., "Olfactory bulb and sensory epithelium in goldfish: Morphological alterations accompanying growth," Ref. No. 78577. Biol Abstr vol. 90, 1990.
Stone et al., "Definition of Regions in Human c-mycThat are Involved in Transformation and Nuclear Localization," Molecular and Cellular Biology vol. 7, No. 5, pp. 1697-1709, 1987.
Svendsen, C.N. & Rosser, A.E., "Neurones from stem cells?" Trends in Neuroscience vol. 18, No. 11, pp. 465-466 (1995).
Svendsen, C.N., Fawcett, J.W., Bentlage, C. & Dunnett, S.B., "Increased survival of rat EGF-generated CNS precursor cells using B27 supplemented medium," Exp. Brain Res. 102: 407-414 (1995).
Svendsen, C.N. et al., "Survival and Differentiation of Rat and Human Epidermal Growth Factor-Responsive Precursor Cells Following Grafting into the Lesioned Adult Central Nervous System," Experimental Neurology 137, 376-388 (1996).
Svendsen, C.N. et al., "A new method for the rapid and long term growth of human neural precursor cells," Journal of Neuroscience Methods 85 (1998) 141-152.
Takahashi J. et al., "Retinoic acid and neurotrophins collaborate to regulate neurogenesis in adult-derived neural stem cell cultures," J Neurobiol, vol. 38, pp. 65-81, 1999.

Takahashi, T. et al., "Cell cycle kinetics of the E14 murine cerebral ventricular zone: estimates based upon S-Phase labeling with BUdR," Society for Neuroscience Abstracts, vol. 16, p. 1147, 1990.
Takeichi, M. et al., "Roles of Magnesium and Calcium Ions in Cell-to-Substrate Adhesion," Experimental Cell Research 74 (1972) 51-60.
Taupin P, et al., "FGF-2-responsive neural stem cell proliferation requires CCg, a novel autocrine/paracrine cofactor," Neuron, vol. 28, pp. 385-397, 2000.
Taylor, M. et al., "Induction of Differentiation of Rat Retinal, Germinal, Neuroepithelial Cells by dbcAMP," Journal of Neurobiology, vol. 21, pp. 470-481, 1990.
Temple, S., "Division and Differentiation of Isolated CNS Blast Cells in Microculture," Nature, vol. 340, pp. 471-473—1989.
Temple, S. et al., "Vertebrate neural progenitor cells: subtypes and regulation," Neurobiology 1996, 6:11-17.
Tenot, M. et al., Epidermal Growth Factor Enhances the Expression of an Edogenous Lectin in Aggregating Fetal Brain Cell Cultures, Journal of Neurochemistry, vol. 53, pp. 1435-1441, 1989.
Tohyama et al., "Nestin Expression in Embryonic Human Neuroepithelium and in Human Neuroepithelial Tumor Cells," Laboratory Investigation 66:3 303-313 (1992).
Torelli, S. et al., "Human Fetal Brain Cultures: A Model to Study Neural Proliferation, Differentiation and Immunocompetence," Adv. Exp. Med. Biol, vol. 296, pp. 121-134, 1991.
Torres, R.A. et al., "Alteration of Neuronal Regulation of Astrocytoma Proliferation by Insertional Mutagenesis," Society for Neuroscience Abstracts, vol. 16, p. 1147, 1990.
Trenkner et al., "Cell Reaggregation and Migration, Fiber and Synapse Formation," The Journal of Cell Biology 75:915-940 (1977).
Tropepe, V. et al., "Direct Neural Fate Specification from Embryonic Stem Cells: A Primitive Mammalian Neural Stem Cell Stage Acquired through a Default Mechanism," Neuron, vol. 30, 65-78, Apr. 2001.
Turner M.R. et al., "Abnormal cortical excitability in sporadic but not homozygous D90A SOD I ALS," J Neurol Neurosurg Psychiatry, vol. 76, pp. 1279-1285, 2005.
Unsicker et al., "Growth factor function in the development and maintenance of midbrain dopaminergic neruons: concepts, facts and prospects for TGF-$\beta$," Ciba Found. Symp. 196, pp. 70-84 (1996.
Van Praag et al., "Running enhances neurogenesis, learning, and long-term potentiation in mice," PNAS, vol. 96, pp. 13427-13431, 1999.
Van Praag et al., "Running increases cell proliferation and neurogenesis in the adult mouse dentate gyrus," Nature Neuroscience, vol. 2, pp. 266-270, 1999.
Vescovi et al., "Isolation and Cloning of Multipotential Stem Cells from the Embryonic Human CNS and Establishment of Transplantable Human Neural Stem Cell Lines by Epigenetic Stimulation," (1999) Exp. Neurol. 156, 71-83.
Vescovi, A.L., Reynolds, B.A., Fraser, D.D., and Weiss, S., "bFGF Regulates the Proliferative Fate of Unipotent (Neuronal) and Bipotent (Neuronal/Astroglial) EGF-Generated CNS Progenitor Cells," Neuron vol. 11, pp. 951-966 (1993).
Vicario-Abejon, C., Johe, K., Hazel, T., Collazo, D. & McKay, R., "Functions of Basic Fibroblast Growth Factor and Neurotrophins in the Differentiation of Hippocampal Neurons," Neuron vol. 15, 105-114 (1995).
Von Frijtag, J. C. et al., "Chronic imipramine treatment partially reverses the !nog-term changes of hipocampal synaptic plasticity in socially stressed rats," Neuroscience Letters, vol. 309, pp. 153-156, 2001.
Von Visger, J.R. et al., "Differentiation and Maturation of Astrocytes Derived from Neuroepithelial Progenitor Cells in Culture," Experimental Neurology 128: 34-40, 1994.
Vu, E.T. et al., "Evidence for a Computational Distinction Between Proximal and Distal Neuronal Inhibition," Science, vol. 255, pp. 1710-1712, 1992.
Wagner et al, "Induction of a midbrain dopaminergic phenotype in Nurr1-overexpressing neural stem cells by type 1 astrocytes,"1999, Nat. Biotech., vol. 17:, pp. 653-659.

(56) References Cited

OTHER PUBLICATIONS

Wainer, B.H. et al., "In vitro cell cultures as model of the basal forebrain," Adv Exp Med Biol., vol. 295, pp. 415-437, 1991.
Wang et al., "A regulatory system for use in gene transfer," (1994) PNAS vol. 91, pp. 8180-8184.
Wang et al., "Induction of dopaminergic neuron phenotype in the midbrain by Sonic hedgehog protein," Nature Medicine, vol. 1, pp. 1184-1188, 1995.
Watanabe, R.T. et al., "Rod Photoreceptor development in vitro: intrinsic properties of proliferating neuroepithelial cells change as development proceeds in the rat retina," NeuralCulture, Abstract, 1990.
Watt et al., "Nucleotide sequence of cloned cDNA of human c-myc oncogene," Nature 303: 725-728, 1983.
Weiss et al., "Multipotent CNS Stem Cells are Present in the Adult Mammalian Spinal Cord and Ventricular Neuroaxis," The Journal of Neuroscience, vol. 16, pp. 7599-7609, 1996.
Weiss et al. reexamination application No. 90/008,580 (reexamination of U.S. Pat. No. 5,851,832) entitled "In Vitro Growth and Proliferation of Multipotent Neural Stem Cells and Their Progeny," filed Apr. 5, 2007.
Weiss et al. reexamination application No. 90/008,367 (reexamination of U.S. Pat. No. 6,294,346) entitled "Use of Multipotent Neural Stem Cells and Their Progeny for the Screening of Drugs and Other Biological Agents," filed Dec. 7, 2006.
Weiss et al. reexamination application No. 90/008,581 (reexamination of U.S. Pat. No. 6,497,872) entitled "Neural Transplantation Using Proliferated Multipotent Neural Stem Cells and Their Prodigy," filed Apr. 5, 2007.
Weiss et al. reexamination application No. 90/008,366 (reexamination of U.S. Pat. No. 7,101,709) entitled "Methods of Screening Biological Agents," filed Dec. 7, 2006.
Weiss, S. et al., "Is there a neural stem cell in the mammalian forebrain?" TINS vol. 19, No. 9, 1996, pp. 387-393.
Weissman, I.L., "Translating Stem and Progenitor Cell Biology to the Clinic: Barriers and Opportunities," Science (2000) 287:1442-1446.
Wohl C A, et al., "Retinoic acid enhances neuronal proliferation and astroglial differentiation in cultures of CNS stem cell-derived precursors," J Neurobiol, vol. 37, pp. 281-290, 1998.
Wolswijk et al., "Identification of an adult-specific glial progenitor cell" Development, 105:387-400 (1989).
Xing et al., "Rat nurr1 is prominently expressed in perirhinal cortex, and differentially induced in the hippocampal dentate gyrus by electroconvulsive vs. kindled seizures," Molecular Brain Research, vol. 47, pp. 251-261, 1997.
Xu et al., "The extremem C terminus of progesterone receptor contains a transcriptional repressor domain that functions through a putative corepressor," Proc. Natl. Acad. Sci., vol. 93, pp. 12195-12199, 1996.
Xu, L. et al., "Glucocorticoid receptor and protein/RNA synthesis-dependent mechanisms underlie the control of synaptic plasticity by stress," PNAS, vol. 95, pp. 3204-3208, 1998.

Yamada et al., "NMDA receptor mediated Ca2+ responses in neurons differentiated from p53-/-immortalized Murin neural stem cells," (1999) Neurosci. Letters 264, pp. 165-167.
Yan J. et al., "Differentiation and Tropic/Trophic Effects of Exogenous Neural Precursors in the Adult Spinal Cord," vol. 480, pp. 101-114, 2004.
Yan, J. et al., "Grafted Human Neural Stem (NS) Cells Differentiate Into Neurons, Migrate Long Distance and Project Axons in Spinal Cord and the Roots of Adult Rats," Program No. 150.19, Abstract Viewer/Ininerary Planner. Society for Neuroscience, 2003.
Ye et al., "FGF and Shh Signals Control Dopaminergic and Serotonergic Cell Fate in the Anterior Neural Plate," Cell vol. 93:755-766 (1998).
Yoshimoto, Y. et al, "The Effect of Cool Storage on the Survivability of Intraventricular Rat Fetal Ventral Mesencephalic Graft," Duke Med Cent Lib 34.P 1, p. 208, 1991.
Zeller et al., "The Timely Expression of Myelin Basic Protein Gene in Cultured Rat Brain Oligodendrocytes is Independent of Continuous Neuronal Influences," The Journal of Neuroscience 5:11 2955-2962 (1985).
Zetterström et al., "Cellular expression of the immediate early transcription factors Nurr I and NGF1-B suggests a gene regulatory role in several brain regions including the nigrostriatal dopamine system," Molecular Brain Research, vol. 41, pp. 111-120, 1996.
Zetterström et al., "Dopamine Neuron Agenesis in Nurr1-Deficient Mice," Science 276:248-250 (1997).
Zhang, R. et al, "A nitric oxide donor induces neurogenesis and reduces functional deficits after stroke in rats," Ann. Neurol., vol. 50, pp. 602-611, 2001.
Baetge, E.E., et al., "Neural Stem Cells for CNS Transplantation", Annals New York Academy of Sciences, 695:285-291, (1993).
Gage, F.H., et al., "Isolation, Characterization, and use of Stem Cells From the CNS", Annu. Rev. Neurosci.,18:159-192, (1995).
Villa, A. et al., "Intracellular calcium ion stores in chicken purkinje neurons; Differential distribution of the low affinity-high capacity calcium binding protein, calsequestrin, of calcium ATPase and of the ER luminal protein," Bip. Ref. No. 31830, Biol Abstr vol. 92, 1991.
Usvald Dusan et al. "Analysis of dosing regimen and reproducibility of intraspinal drafting of human spinal stem cells in immunosuppressed minipigs" Cell Transplantation 2010, vol. 19, No. 9, Feb. 1, 2010, pp. 1103-1122, XP009153897.
Naegele J R et al. "Recent advancements in stem cell and gene therapies for neurological disorders and intractable epilepsy", Neuropharmacology, Pergamon Press, Oxford, GB, vol. 58, No. 6, May 1, 2010 (May 1, 2010), pp. 855-864, XP026954340.
Cizkova et al. "Functional recovery in rats with ischemic paraplegia after spinal grafting of human spinal stem cells", Neuroscience, New York, NY, US, vol. 147, No. 2, Jun. 19, 2007, pp. 546-560, XP022122069.
Bersano A. et al. "Clinical Studies in Stem Cells Transplantation for Stroke: A Review" Current Vascular Pharmacology, (2010), vol. 8, pp. 29-34.
European Office Action for European Application No. 11746083.3 mailed May 26, 2014.

\* cited by examiner

METHODS FOR TREATING AND/OR REVERSING NEURODEGENERATIVE DISEASES AND/OR DISORDERS

BACKGROUND

A stroke is the sudden death of brain cells in a localized area due to inadequate blood flow. A stroke occurs when blood flow is interrupted to part of the brain. Without blood to supply oxygen and nutrients and to remove waste products, brain cells quickly begin to die. Depending on the region of the brain affected, a stroke may cause paralysis, speech impairment, loss of memory and reasoning ability, coma, or death.

SUMMARY

The present disclosure relates to methods for treating and/or reversing neurological diseases or disorders associated with neuronal cell loss (e.g., cell death caused by cerebral ischemic stroke, hemorrhagic stroke, cerebral palsy, or traumatic brain injury) in a brain. Such methods may be useful for treating symptoms resulting from stroke or other brain injuries.

The present disclosure also provides methods for treating a disease or disorder associated with neuronal cell loss in a brain including, for example, for treating the symptoms resulting from stroke or other brain injuries, by obtaining an expanded neural stem cell population and introducing a therapeutically effective amount of the expanded neural stem cell population to at least one area of the brain of a subject, wherein the neural stem cell population differentiates into neurons that integrate in vivo into the brain of the subject. Without wishing to be bound by a theory of the invention, it is believed that the integrated neurons then promote repair of the injured tissue by replacing the dead neurons, regenerating the host neurons, and/or inducing plasticity of the host circuitry to re-establish the damaged neuronal connections that include the donor neurons.

In some embodiments, introducing the therapeutically effective amount of the expanded population includes injecting at least a portion of the therapeutically effective amount into one to a plurality of areas of the brain of the subject.

In some embodiments, expanding the at least one neural stem cell includes culturing the neural stem cell in the absence of serum.

In some embodiments, expanding the at least one neural stem cell includes exposing the at least one neural stem cells to at least one growth factor. In some embodiments, the growth factor is selected from the group consisting of bFGF, EGF, TGF-alpha, aFGF and combinations thereof.

In some embodiments, at least 20%, 30%, 40%, 50%, 60%, 70%, 80% or 90% of the expanded stem cell population is capable of generating neurons in brain tissue of the subject.

In some embodiments, introducing the therapeutically effective amount of the expanded stem cell population includes injecting at least a portion of the therapeutically effective amount into a plurality of areas of brain tissue of the subject.

In some embodiments, the areas of the brain involve the motor pathway—the neuronal fibers that conduct electrical signals to and from the brain, brainstem, and spinal cord that govern muscle contraction. Such areas include the motor cortex, striatum, internal capsule, thalamus, midbrain, brainstem, and cerebellum. Due to stroke or trauma, a discrete area or areas within this pathway may be damaged, resulting in symptoms of paralysis, spasticity, rigidity, and other motor dysfunctions.

In another embodiment, a suspension of the spinal cord-derived human neural stem cells are injected into, near, or around the affected area(s). The injected cells differentiate into neurons and glia which integrate into the affected area to promote repair of motor pathway that results in motor recovery and/or amelioration of the motor dysfunction.

In some embodiments, the subject had an event that caused cerebral ischemia such as a heart attack or stroke.

The present disclosure also provides methods for treating stroke in a subject in need thereof comprising isolating at least one neural stem cell from spinal cord tissue of a human; expanding in vitro said neural stem cell to form an expanded population; concentrating the expanded population; and introducing a therapeutically effective amount of said expanded population to at least one area of the subject brain.

In other embodiments, the expanded neural stem cell population is derived from a spinal cord tissue including, for example, a post-mortem fetal spinal cord tissue of a human.

In some embodiments, the gestational age of the post-mortem fetus is between about 5 and about 20 weeks.

In some embodiments, expanding the at least one neural stem cell includes culturing the neural stem cell in the absence of serum.

In some embodiments, expanding the at least one neural stem cell includes exposing the at least one neural stem cells to at least one growth factor. In some embodiments, the growth factor is selected from the group consisting of bFGF, EGF, TGF-alpha, aFGF and combinations thereof.

In some embodiments, at least 20%, 30%, 40%, 50%, 60%, 70%, 80% or 90% of the expanded stem cell population is capable of generating neurons in brain tissue of the subject.

In some embodiments, introducing the therapeutically effective amount of the expanded stem cell population includes injecting at least a portion of the therapeutically effective amount into a plurality of areas of brain tissue of the subject.

These and other embodiments of the invention are described in further detail herein below.

BRIEF DESCRIPTION OF THE DRAWINGS

The foregoing summary, as well as the following detailed description of the disclosure, will be better understood when read in conjunction with the appended figures.

DETAILED DESCRIPTION

The disclosed methods are related to the treatment of neurological diseases or disorders associated with neuronal cell loss in the brain. It has now been discovered that a human spinal cord stem cell line (HSSC), when transplanted into a peri-infarct area in the brain, was able to survive and differentiate en mass into neurons in the damaged tissue. Notably, the differentiated neurons integrated (i.e. established interconnectivity with other neurons) into the surrounding brain tissue and reversed motor deficits. As such, the methods of the disclosure may be used to treat including, reverse, neurodegenerative diseases including, for example, diseases of the brain. In particular, the methods of the disclosure may be used to treat any motor symptom (e.g., paresis, paralysis, spasticity or rigidity) arising from cerebral ischemia. The motor symptoms may be in acute, subacute, or chronic phases of the disease (e.g., in chronic stroke).

The present disclosure provides methods for treating and/or reversing a neurological or neurodegenerative disease or disorder associated with neuronal cell loss (e.g., cell death) in a brain (e.g., a brain tissue such as cerebral hemispheres, cerebral cortex, subcortex motor cortex, striatum, internal capsule, thalamus, hypothalamus, hippocampus, midbrain, brainstem, and cerebellum) by obtaining an expanded neuronal stem cell population (e.g., a human spinal cord stem cell line) and introducing a therapeutically effective amount of the expanded neuronal stem cell population to one to a plurality of areas of the brain of a subject, wherein the neuronal stem cell population is capable of differentiating into neurons that integrate in vivo into the brain of the subject.

The present disclosure also provides methods of treating and/or reversing paresis, paralysis, spasticity, rigidity or muscular hyperactivity conditions associated with cerebral ishcemia in a subject in need thereof by isolating at least one neural stem cell (e.g., a human spinal cord stem cell line) from a mammal; expanding in vitro said neural stem cell to an expanded population; concentrating the expanded population; and introducing a therapeutically effective amount of said expanded population to at least one area of the subject brain (e.g., a brain tissue such as cerebral hemispheres, cerebral cortex, subcortex motor cortex, striatum, internal capsule, thalamus, hypothalamus, hippocampus, midbrain, brainstem, and cerebellum). In one embodiment, at least 20% of the expanded population is capable of generating neurons in the subject brain.

The disclosed methods include the use of NSCs to ameliorate a neurodegenerative condition. As used herein, the term, "NSCs" can also refer to neural or neuronal progenitors, or neuroepithelial precursors. NSCs can be functionally defined according to their capacity to differentiate into each of the three major cell types of the CNS: neurons, astrocytes, and oligodendrocytes.

In some embodiments, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms.

In some embodiments, "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (A) or Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician.

In one embodiment, the NSCs are multipotential such that each cell has the capacity to differentiate into a neuron, astrocyte or oligodendrocyte. In another embodiment, the NSCs are bipotential such that each cell has the capacity to differentiate into two of the three cell types of the CNS. In another embodiment, the NSCs include at least bipotential cells generating both neurons and astrocytes in vitro and include at least unipotential cells generating neurons in vivo.

Growth conditions can influence the differentiation direction of the cells toward one cell type or another, indicating that the cells are not committed toward a single lineage. In culture conditions that favor neuronal differentiation, cells, particularly from human CNS, are largely bipotential for neurons and astrocytes and differentiation into oligodendrocytes is minimal. Thus, the differentiated cell cultures of the disclosed methods may give rise to neurons and astrocytes. In one embodiment, the ratio of neurons to astrocytes is about 20:80 to about 80:20, for example about 50:50.

In one embodiment of the disclosed methods, the cells to be transplanted into subjects are derived from brain tissue. In another embodiment, NSCs are isolated from human fetal brain tissue at gestational ages of between about 5 to about 20 weeks. It should be appreciated that the proportion of the isolatable neural stem cell population can vary with the age of the donor. Expansion capacity of the cell populations can also vary with the age of the donor. Such regional and temporal specificity of NSCs indicates that NSCs behave as fate-restricted progenitors and not as blank cells or a single population of cells.

The NSCs of the ventral midbrain, for example, are distinct from the NSCs obtained from the spinal cord at the same gestational stage. In particular, the NSCs from the ventral midbrain exclusively give rise to tyrosine-hydroxylase-expressing dopaminergic neurons, whereas NSCs from the spinal cord exclusively generate acetylcholine-producing cholinergic neurons. Both cell types, however, simultaneously generate the more ubiquitous gluamate- and GABA-producing neurons. Therefore, in an embodiment, the disclosed methods include obtaining NSCs from the ventral midbrain to treat conditions ameliorated or attenuated, at least in part, by the implantation of tyrosine-hydroxylase-expressing dopaminergic neurons.

NSCs can also be isolated from post-natal and adult tissues. NSCs derived from post-natal and adult tissues are quantitatively equivalent with respect to their capacity to differentiate into neurons and glia, as well as in their growth and differentiation characteristics. However, the efficiency of in vitro isolation of NSCs from various post-natal and adult CNS can be much lower than isolation of NSCs from fetal tissues which harbor a more abundant population of NSCs. Nevertheless, as with fetal-derived NSCs, the disclosed methods enable at least about 30% of NSCs derived from neonatal and adult sources to differentiate into neurons in vitro. Thus, post-natal and adult tissues can be used as described above in the case of fetal-derived NSCs.

Various neuronal subtypes can be obtained from manipulation of embryonic stem cells expanded in culture. Thus, specific neuronal subtypes, based on the disclosed methods, can be isolated and purified from other irrelevant or unwanted cells to improve the result, as needed, and can be used for treatment of the same neurodegenerative conditions.

The NSCs in the disclosed methods can be derived from one site and transplanted to another site within the same subject as an autograft. Furthermore, the NSCs in the disclosed methods can be derived from a genetically identical donor and transplanted as an isograft. Still further, the NSCs in the disclosed methods can be derived from a genetically non-identical member of the same species and transplanted as an allograft. Alternatively, NSCs can be derived from non-human origin and transplanted as a xenograft. With the development of powerful immunosuppressants, allograft and xenograft of non-human neural precursors, such as neural precursors of porcine origin, can be grafted into human subjects.

A sample tissue can be dissociated by any standard method. In one embodiment, tissue is dissociated by gentle mechanical trituration using a pipette and a divalent cation-free buffer (e.g. saline) to form a suspension of dissociated cells. Sufficient dissociation to obtain largely single cells is desired to avoid excessive local cell density.

For successful commercial application of NSCs, maintaining robust and consistent cultures that have stable expansion and differentiation capacities through many successive passages is desirable. As described above, the culture methods can be optimized to achieve long-term, stable expansion of an individual cell line of NSCs from different areas and ages of CNS development while maintaining their distinct progenitor properties. In one embodiment, stem cells can be cultured according to the methods set forth in U.S. Pat. No. 7,691,629, U.S. Pat. No. 5,753,506, U.S. Pat. No. 6,040,180, or U.S. Pat. No. 7,544,511, the entireties of which are incorporated by reference herein.

In an embodiment, the NSCs of the disclosed methods can include pre-differentiated cells for transplantation. For maximum yield of the cells and for simplicity of the procedure, a confluent culture is harvested for transplantation which comprises primarily a population of undifferentiated cells. It should be appreciated, however, that a minor population of cells just starting to differentiate spontaneously can also exist due to the increased cell density.

In an embodiment, the NSCs are concentrated in a solution such as the clinically usable, hibernation or freezing solutions described above. In an embodiment, the NSCs are concentrated to an appropriate cell density which can be the same or different from the cell density for administration of the cells. In an embodiment, the cell density for administration can vary from about 1,000 cells per microliter to about 1,000,000 cells per microliter depending upon factors such as the site of the injection, the neurodegenerative status of the injection site, the minimum dose necessary for a beneficial effect, and toxicity side-effect considerations. In an embodiment, the disclosed methods include injecting NSCs at a cell density of about 5,000 to about 50,000 cells per microliter.

The volume of media in which the expanded NSCs are suspended for delivery to a treatment area can be referred to herein as the injection volume. The injection volume depends upon the injection site and the degenerative state of the tissue. More specifically, the lower limit of the injection volume can be determined by practical liquid handling of viscous suspensions of high cell density as well as the tendency of the cells to cluster. The upper limit of the injection volume can be determined by limits of compression force exerted by the injection volume that are necessary to avoid injuring the host tissue, as well as the practical surgery time.

Low cell survival of donor cells using known methods has necessitated the delivery of a large quantity of cells to a relatively small area in order to attempt effective treatment. Injection volume, however, is hydrostatic pressure exerted on the host tissue and the prolonged injection time associated with high injection volumes exacerbates surgical risk. Additionally, over-injection of donor cells leads to compression and subsequent injury of the host parenchymal tissue. In attempting to compensate for volume constraints, known methods have required preparation of high cell density suspensions for the injections. However, a high cell density promotes tight clustering of the transplanted cells and inhibits cell migration or spreading preventing effective treatment beyond a limited area and compromising seamless integration into the host tissue.

In contrast, as a result of improved survival in vivo of the cells prepared by the disclosed methods, fewer number of cells are needed per injection. In fact, up to three to four times the number of injected cells have been shown to exist after six months from the time of injection demonstrating significant quantitative survival using the disclosed methods. Also, because of the quantitative survival, reproducible administration of desired cell doses can be achieved. Accordingly, in one embodiment, the NSCs are concentrated to a density of about 1,000 to about 200,000 cells per microliter. In another embodiment, about 5,000 to about 50,000 NSCs per microliter have been used for effective engraftment. In another embodiment, about 10,000 to 30,000 NSCs per microliter are used. In another embodiment, the NSCs can be delivered to a treatment area suspended in an injection volume of less than about 100 microliters per injection site. For example, in the treatment of neurodegenerative conditions of a human subject where multiple injections may be made, an injection volume of 0.1 and about 100 microliters per injection site can be used.

Any suitable device for injecting the cells into a desired area can be employed in the disclosed methods. In an embodiment, a syringe capable of delivering sub-microliter volumes over a time period at a substantially constant flow rate is used. The cells can be loaded into the device through a needle or a flexible tubing or any other suitable transfer device.

In one embodiment, the desired injection site for treatment of a neurodegenerative condition includes at least one area of the brain. In another embodiment, the cells are implanted into at least one specific segment or region of the brain such as the cerebral cortex, cerebral hemispheres, thalamus, hypothalamus, midbrain, cerebellum, pons, or medulla oblongata.

In another embodiment, the cells are injected at between about 5 and about 50 sites in the brain. In an embodiment, the cells are injected at between about 10 to about 30 sites in the brain. At least two of the sites can be separated by a distance of approximately 100 microns to about 5000 microns. In an embodiment, the distance between injection sites is about 400 to about 600 microns. The distance between injections sites can be determined based on generating substantially uninterrupted and contiguous donor cell presence throughout the brain tissue and based on the average volume of injections demonstrated to achieve about 2-3 month survival in animal models such as rats or pigs. The actual number of injections in humans can be extrapolated from results in animal models.

The NSCs of the disclosed methods can generate large numbers of neurons in vivo. When the NSCs are not overtly pre-differentiated prior to transplant, the NSCs can proliferate up to two to four cell divisions in vivo before differentiating, thereby further increasing the number of effective donor cells. Upon differentiation, the neurons secrete specific neurotransmitters. In addition, the neurons secrete into the mileu surrounding the transplant in vivo growth factors, enzymes and other proteins or substances which are beneficial for different conditions. Accordingly, a variety of conditions can be treated by the disclosed methods because of the ability of the implanted cells to generate large numbers of neurons in vivo and because the neurodegenerative conditions may be caused by or result in missing elements including neuron-derived elements. Therefore, subjects suffering from degeneration of CNS tissues due to lack of such neuron-derived elements, such as growth factors, enzymes and other proteins, can be treated effectively by the disclosed methods.

The disclosed methods can also be applied to treat paresis, paralysis, spasticity, rigidity or any other motor, speech, or cognitive symptoms arising from cerebral ischemia. Cerebral ischemia can occur as a result of a stroke event in the brain or from a heart attack in which the blood circulation to the brain is interrupted for a significant period of time. It is, thus, analogous to the spinal cord ischemia described above. Some stroke subjects develop seizures of central origin as well as other deficits such as memory loss, paralysis, or paresis. These deficits from cerebral ischemia are also likely due to selective loss of inhibitory interneurons in hippocampus and/or other brain areas. Thus, the disclosed methods can be applied to treat stroke subjects suffering from paresis, paralysis, spasticity, or other motor, speech, and cognitive symptoms.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Expansion of Human Spinal Cord Neural Stem/Progenitor Cells

Spinal cord from at least one donor of gestational age of approximately 7-8.5 weeks was obtained. A single contiguous tissue of the spinal cord was dissociated in $Ca^{++}$ and $Mg^{++}$-free phosphate buffered saline using mechanical trituration. The resulting cell suspension was then seeded into tissue culture plates pre-coated with both poly-L-ornithine or poly-D-lysine and human fibronectin or other extracellular matrix proteins. Tissue culture-treated plates or flasks were then incubated with 100 μg/ml poly-D-lysine for 1 hour at room temperature. They were then washed three times with water and dried. They were then incubated with 25 mg/ml fibronectin for 5 minutes at room temperature. Sometimes, 10 mg/ml fibronectin for 1 hour at room temperature was used. Sometimes, 1 mg/ml fibronectin for 18 hours at 37° C. was used. Culture media consisting of N2 (DMEM/F12 plus insulin, transferrin, selenium, putrescine, and progesterone) was supplemented with 1 human recombinant basic fibroblast growth factor (bFGF). In an embodiment, a range of 0.1 ng/ml-100 ng/ml can be used. In an embodiment, optimally, 10 ng/ml of bFGF was used.

The resulting initial culture consists of post-mitotic neurons and proliferative NSCs in a monolayer. Subsequently, after approximately five to about twenty days in culture, the dividing, nestin-positive, NSCs dominate the culture over the non-dividing neurons or the slowly-dividing glia. Under these culture conditions, NSCs are selectively favored for expansion. The expanding NSC population was passaged by mild enzymatic treatment, such as using trypsin. The cells were then cultured in media free of serum or substantially free of serum. Although low concentration of serum may be tolerated by the cells, it is best to avoid exposing the cells to serum since serum contains many cytokines such as LIF and CNTF which promote glial differentiation of the NSCs. Thus, during passage, the enzyme used was stopped by adding specific enzyme inhibitor, such as trypsin inhibitor, rather than serum. At each passage, the number of harvested cells were counted, and a fraction was re-seeded for further expansion. Using this method, human NSCs can be expanded beyond $10^{18}$-fold increase in population while maintaining their growth and differentiation properties. During the expansion, almost all cells express nestin, the in vivo marker of mitotic neuroepithelial cells, and are absent of antigens of differentiated neurons and glia such as type 3-beta tubulin and GFAP. The cells were also negative by immunostaining for PSA-NCAM, a possible marker of committed neuronal progenitors, O4 and GalC, markers of oligodendrocytes, and RC2, a marker of radial glia. Thus, determined by immunostaining, the NSCs stably maintain their expression of antigen profile throughout the prolonged expansion period.

Example 2

Differentiation of Human Spinal Cord Neural Stem/Progenitor Cells

At any point during expansion of the NSCs, the cultures can be differentiated by withdrawal of the mitogen in the culture such as bFGF. Differentiation of NSCs ensues within about 1-3 days after the removal of mitogen, and distinct heterogeneous cell morphologies are apparent. By approximately day 4-7 of differentiation, neuron-specific antigens, such as MAP2c, tau, and type III beta-tubulin, can be visualized by immunostaining. By approximately day 12-14, elongated, fasciculated axonal processes are evident throughout the culture along with clear polarization of subcellular protein trafficking. By approximately day 28, synaptic proteins, such as synapsin and synaptophysin, localize into axon terminals, appearing as punctate staining. Additional feeder layer of astrocytes can be provided to further promote long-term maturation of the neurons. Differentiation of human spinal NSCs generates mixed cultures of neurons and glia wherein the neurons robustly express neuron-specific antigens such as tau, MAP2ab and type3 beta tubulin and comprises approximately 50% of the culture. Additionally, the culture spontaneously generates long, bundled, axon cables that stretch for several centimeters. A significant proportion of the neurons are GABAergic with cholinergic motor neurons also being present in the culture. Presence of significant GABA neurons in culture predicts usefulness of the human spinal NSCs for treating various neurological conditions caused by decreased GABA production in certain circuitry. Likewise, presence of cholinergic neurons demonstrates that the human spinal NSCs are capable of motor neuron differentiation and predicts their usefulness for treating various motor neuron diseases caused by gradual degeneration of motor neurons. For treatment, the NSCs may be expanded with or without further phenotype-enhancing conditions, harvested, and injected into a neural area of deficiency.

Example 3

Transplantation of Spinal-Cord Derived Neural Stem Cells to the Brain

A neuronal stem cell may be isolated from a mammal expanded in vitro and then introduced (e.g., transplanted) to one or more areas in a subject (e.g., a subject's brain) afflicted with a neurodegenerative disease and/or disorder.

In an exemplary method for treatment of a neurodegenerative disorder, cerebral ischemia (e.g., a stroke) was induced in adult male Sprague-Dawley rats (weighing 250-300 g) on day 0 by subjecting the rats to three-vessel ligation by modified methods described previously (see, Chen et al., 1986; Shyu et al. 2004). Briefly, rats were anesthetized with chloral hydrate (0.4 g/kg, ip) and bilateral CCAs were clamped with non-traumatic arterial clips. Next, using a surgical microscope, a 2×2 mm craniotomy was drilled where the zygoma fuses to the squamosal bone. The right MCA was then ligated with an I0-O nylon suture. Cortical blood flow was measured continuously with a laser Doppler flowmeter (PF-5010, Periflux system, Perimed AB, Stockholm, Sweden) in anesthetized rats. Next, a burr hole (1-mm diameter) was made in the right frontoparietal region to allow placement of photodetectors. A probe (0.45 mm in diameter) was then stereotaxically placed in the cortex (1.3 mm posterior, 2.8 mm lateral to the bregma, and 1.0 mm below the dura). After 90 minutes of ligation, the suture on the MCA and arterial clips on CCAs were then removed to allow reperfusion. While rats were under anesthesia, their core body temperature was monitored with a thermistor probe and maintained at 37° C. with a heating pad during anesthesia. After recovery from anesthesia, body temperature was maintained at 37° C. with a heat lamp.

Next, the rats subjected to three-vessel ligation procedure were divided into two groups. The first group ("transplantation group") received NSI-566RSC cells (a human spinal stem cell line, "HSSC" line; clinical lot, Neuralstem, Inc., USA) and the second group ("control group") received a vehicle-control. The NSI-566RSC stem cell line was derived from a fetal spinal cord tissue. Stem cells from a cGMP clinical lot (passage 12) were used in this study. On the day of surgery, one cryopreserved vial of the cells was thawed, washed, and concentrated according to Neuralstem's protocol. All animals in the study received a once daily injection of FK506 (or Prograf) at 1 mg/kg i.p. to suppress their immune system.

NSI-566RSC cells or control vehicle was administered on day 7 to the transplantation and control group, respectively. Rats in the transplantation group were injected stereotaxically with approximately $2×10^5$ NSI-566RSC cells in a 5 µl suspension through a 30-gauge Hamilton syringe into 3 subcortical areas, 3.0 to 5.0 mm below the dura. The approximate coordinates for these sites were 1.0 to 2.0 mm anterior to the bregma and 3.5 to 4.0 mm lateral to the midline, 0.5 to 1.5 mm posterior to the bregma and 4.0 to 4.5 mm lateral to the midline, and 3.0 to 4.0 mm posterior to the bregma and 4.5 to 5.0 mm lateral to the midline. The needle was retained in place for 5 minutes after each injection and a piece of bone wax is applied to the skull defects to prevent leakage of the injected solution. Experimental rats in the vehicle-control group were treated stereotaxically with the suspension buffer only without the cells.

Figure 1:
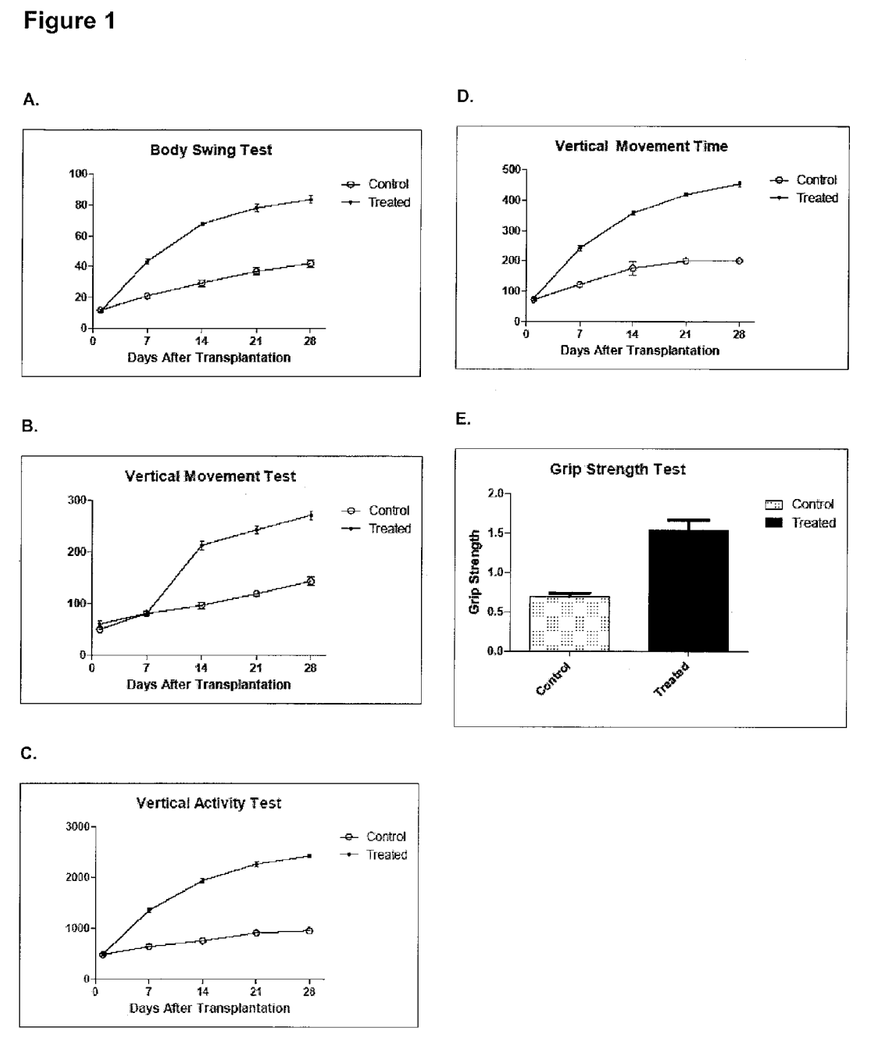
FIG. 1 shows that transplantation of human spinal-cord derived neural stem cells (HSSC) improved neurological behavior after cerebral ischemia. Neurological behavior measurement protocols were used to assess neurological function before and after MCA ligation in HSSC-implanted rats (n=10) and buffer-injected control rats (n=10). HSSC rats exhibited significantly reduced body asymmetry in comparison with control rats in a body swing test (Panel A). Locomotor activity was examined before and after cerebral ischemia in all animals. Vertical activity, vertical movement time, and the number of vertical movements showed a significant increase after cerebral ischemia in rats receiving HSSC transplantation in comparison with control rats (Panels B-D). Furthermore, measurement of grip strength was performed to examine the forelimb strength of all experimental rats after each of the two treatments (Panel E). The results revealed a higher ratio of grip strength in the HSSC group than in the control groups.

Neurological behavioral assessments were performed 3 days before cerebral ischemia, and day 1, 7, 14, 21 and 28 after treatment. The tests measured (a) body asymmetry, (b) locomotor activity and (c) grip strength. Pre-treatment scores were recorded in order to normalize those taken after cerebral ischemia. For body asymmetry, the elevated body swing test (EBST) was used to assess body asymmetry after MCA ligation and evaluated quantitatively, as previous described (Borlongan et al., 1998). Initially, animals were examined for lateral movement, with their bodies suspended by their tails. The frequency of initial head swing contralateral to the ischemic side was counted in twenty continuous tests and normalized, as previously described (Chang et al., 2003) (FIG. 1, Panel A). For locomotor activity, rats were subjected to VersaMax Animal Activity monitoring (Accuscan Instruments, Inc., Columbus, Ohio) for about 2 hours for behavioral recording of each of the experimental rats. The VersaMax Animal Activity monitor contains 16 horizontal and 8 vertical infrared sensors spaced 87 cm apart. The vertical sensors are situated 10 cm from the floor of the chamber. Locomotor activity was counted as the number of beams broken by a rat's movement in the chamber. Three vertical parameters defined in the manufacturer's menu option were calculated over 2 hours at night: (i) vertical activity, (ii) vertical time, and (iii) number of vertical movements (FIG. 1, Panels B-D). For grip strength, rats were analyzed using a Grip Strength Meter (TSE-Systems, Germany) as previously described, with modification (Dunnett et al., 1998). In brief, the grip strength ratio of each forelimb was measured separately and calculated as the ratio between the mean strength out of 20 pulls of the side contralateral to the ischemia and that of ipsilateral side. In addition, the ratio of grip strength post-treatment and prior to treatment were also calculated and changes were presented as a percentage of the pre-treatment value (FIG. 1, Panel E). Overall, the investigators were blinded when measuring behavioral changes in the cell-treated and control group.

Figure 2A:
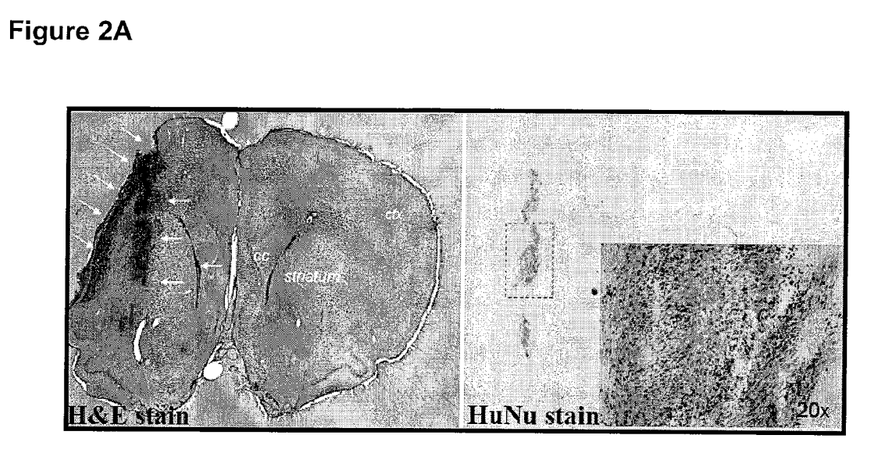
FIGS. 2A-B shows images obtained from an immunohistochemical (IHC) analysis of exogenously transplanted HSSC engrafted in the ischemic rat brain. The penumbra of HSSC-treated ischemic rat brains were immunostained with antibodies for human specific nuclear antibody (HuNu) (FIG. 2A) and neuronal specific enolase (NSE) (FIG. 2B).
Figure 2B:
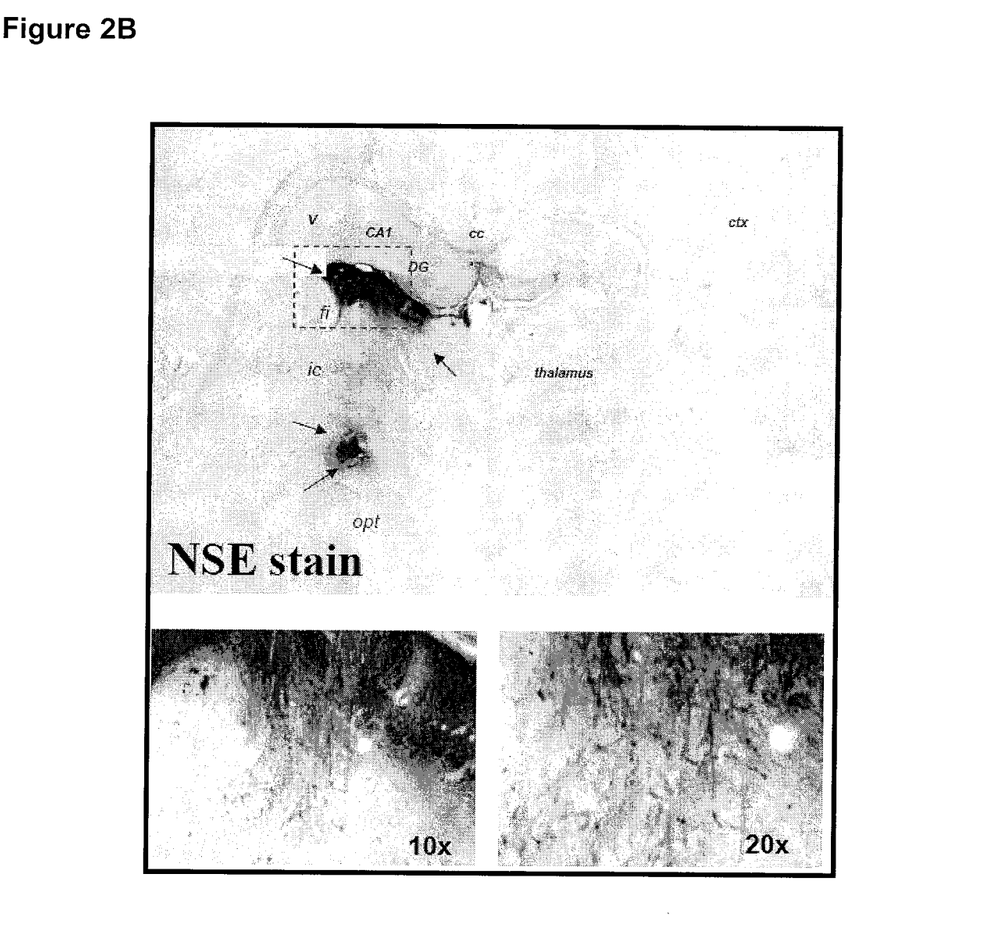

Approximately twenty-seven days after the rats were subjected to the three-vessel ligation procedure, rats were anesthetized with chloral hydrate (0.4 g/kg, ip) and their brains fixed by transcardial perfusion with saline, followed by perfusion and immersion in 4% paraformaldehyde, before being removed and embedded in 30% sucrose. A series of adjacent 20-μm-thick sections were cut from each brain in the coronal plane, stained with H&E and observed by light microscopy (Nikon, E600, Japan). Human grafted cells were then identified by various human-specific antibodies (HuNu, synptophysin, hNSE, hNF, and others) (see, FIGS. 2A-2B). For BrdU immunostaining, DNA is first denatured by incubating each section in 50% formamide of 2× standard saline citrate at 65° C. for 2 hours, then in 2 N HCl at 37° C. for 30 minutes, and finally rinsed in 0.1 M boric acid with pH 8.5. Next, sections were rinsed with Tris buffer and treated with 1% $H_2O_2$ to block endogenous peroxidase. The immunostaining procedure was then performed using the labeled streptavidin-biotin (LSAB) method (DAKO LASB-2 Kit, Peroxidase, DAKO, USA). Brain tissue, on a silane-coated slide, was then placed in boiling citrate buffer (pH 6, ChemMate, DAKO, USA) twice for 5 minutes in a microwave oven at 750 W, after deparaffinization and rehydration. Next, tissues were incubated with the appropriate diluted primary antibodies to BrdU (for nuclear identification, dilution 1:400, Sigma, USA), at room temperature for 1 hour. After washing with Tris-buffered saline, containing 0.1% Tween-20 (TBS-T), the specimens were sequentially incubated for 10 to 30 minutes with biotinylated anti-rabbit and anti-mouse (1:200, R&D Systems, USA) immunoglobulins and peroxidase-labeled streptavidin. Staining was performed after a 10 minute incubation with a freshly prepared substrate-chromogen solution, containing 3% 3-amino-9-ethylcarbazole and hydrogen peroxide. Finally, the slides were lightly counterstained with hematoxylin, washed with water, and then mounted. Negative control sections were stained with identical preparations of brain tissue specimen, except that primary antibodies were omitted. Quantification of BrdU immunoreactive cells were counted digitally using a 60× objective lens (Carl Zeiss LSM510, Germany) via a computer imaging analysis system (Imaging Research, Canada).

Additionally, cell type-specific markers co-localized with exogenous transplanted NPCs and endogenous homing stem cells (BrdU immunoreactive), may be identified by immunofluorescent colocalization analysis by laser-scanning confocal microscopy. In immuno-fluorescent colocalization studies, each coronal section is treated with cell-specific antibodies, for example, glial fibrillary acidic protein (GFAP for astrocyte, 1:400, Sigma, USA), Von-Willebrand factor (vWF for endothelial cell, 1:400, Sigma, USA), neuronal nuclear antigen (Neu-N for neuronal nuclei, 1:200, Chemicon, CA), Nestin (for neuronal dendrites, 1:200, Chemicon, CA), microtubule-associated protein 2 (MAP-2 for neuronal dendrites, 1:200; BM, Germany), stromal cell-derived factor 1 (SDF-1, 1:200) and CXC receptor type 4 (CXCR4, 1:200) from Chemokine, and $PrP^C$ (1:300; M20, Santa Cruz). with Cy3 (Jackson Immunoresearch PA USA, 1:500, USA) staining.

As shown in FIG. 1, animals treated with NSI-566RSC cells exhibited improvements in body swing, vertical movement, vertical activity, vertical movement time, and grip strength compared to animals treated with control vehicle.

Aspects, including embodiments, of the present subject matter described above may be beneficial alone or in combination, with one or more other aspects or embodiments. Without limiting the foregoing description, in accordance with one aspect of the subject matter herein, there is provided methods for treating a disease or disorder associated with neuronal cell loss in a brain, the methods comprising: obtaining at least one stem cell from spinal cord tissue of a human; expanding the at least one stem cell to form an expanded stem cell population; and introducing a therapeutically effective amount of the expanded stem cell population to at least one area of the brain of a subject.

In accordance with another aspect which may be used or combined with any of the preceding or following aspects, the expanded stem cell population differentiates into neurons that integrate in vivo into the brain of the subject.

In accordance with another aspect which may be used or combined with any of the preceding or following aspects, the disease or disorder is caused by cerebral ischemia, hemorrhage, and trauma.

In accordance with another aspect which may be used or combined with any of the preceding or following aspects, the disease or disorder involves paralysis, speech impairment, loss of memory, or reasoning ability.

In accordance with another aspect which may be used or combined with any of the preceding or following aspects, the disease or disorder involves motor dysfunction or cognitive deficit.

In accordance with another aspect which may be used or combined with any of the preceding or following aspects, the human has a gestational age of about 5 to about 20 weeks.

In accordance with another aspect which may be used or combined with any of the preceding or following aspects, expanding the at least one neural stem cell includes culturing the neural stem cell in absence of serum.

In accordance with another aspect which may be used or combined with any of the preceding or following aspects, expanding the at least one neural stem cell includes exposing the at least one neural stem cell to at least one growth factor.

In accordance with another aspect which may be used or combined with any of the preceding or following aspects, the growth factor is selected from the group consisting of bFGF, EGF, TGF-alpha, aFGF and combinations thereof.

In accordance with another aspect which may be used or combined with any of the preceding or following aspects, at least 20%, 30%, 40%, 50%, 60%, 70%, 80% or 90% of the expanded stem cell population is capable of generating neurons in brain tissue of the subject.

In accordance with another aspect which may be used or combined with any of the preceding or following aspects, at least 20%, 30%, 40%, 50%, 60%, 70%, 80% or 90% of the expanded stem cell population is capable of differentiating into neurons in vitro.

In accordance with another aspect which may be used or combined with any of the preceding or following aspects, introducing the therapeutically effective amount of the expanded stem cell population includes injecting at least a portion of the therapeutically effective amount into a plurality of areas of brain tissue of the subject.

In accordance with another aspect which may be used or combined with any of the preceding or following aspects, the areas include cerebral hemispheres, cerebral cortex, subcortex motor cortex, striatum, internal capsule, thalamus, hypothalamus, hippocampus, midbrain, brainstem, and cerebellum.

In accordance with another aspect which may be used or combined with any of the preceding or following aspects, the subject experienced an event that caused cerebral ischemia.

In accordance with another aspect which may be used or combined with any of the preceding or following aspects, the event is a stroke.

Without limiting the foregoing description, in accordance with another aspect of the subject matter herein, there is provided methods of treating stroke in a subject in need thereof, the methods comprising: isolating at least one neural stem cell from spinal cord tissue of a human; expanding in vitro said neural stem cell to form an expanded population; concentrating the expanded population; and introducing a therapeutically effective amount of said expanded population to at least one area of the subject brain.

In accordance with another aspect which may be used or combined with any of the preceding or following aspects, the spinal cord is from a gestation age of about 5 to about 20 weeks.

In accordance with another aspect which may be used or combined with any of the preceding or following aspects, expanding the at least one neural stem cell includes culturing the neural stem cell in absence of serum.

In accordance with another aspect which may be used or combined with any of the preceding or following aspects, expanding the at least one neural stem cell includes exposing the at least one neural stem cell to at least one growth factor.

In accordance with another aspect which may be used or combined with any of the preceding or following aspects, the growth factor is selected from the group consisting of bFGF, EGF, TGF-alpha, aFGF and combinations thereof.

In accordance with another aspect which may be used or combined with any of the preceding or following aspects, at least 20%, 30%, 40%, 50%, 60%, 70%, 80% or 90% of the expanded population is capable of generating neurons in brain tissue of the subject.

In accordance with another aspect which may be used or combined with any of the preceding or following aspects, introducing the therapeutically effective amount of the expanded population includes injecting at least a portion of the therapeutically effective amount into one to a plurality of areas of the recipient brain.

In accordance with another aspect which may be used or combined with any of the preceding or following aspects, the areas of the recipient brain include cerebral hemispheres, cerebral cortex, subcortex motor cortex, striatum, internal capsule, thalamus, hypothalamus, hippocampus, midbrain, brainstem, and cerebellum.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method for inhibiting or relieving a disease or disorder associated with neuronal cell loss in a brain, said method comprising: a) obtaining at least one stem cell from spinal cord tissue of a human having a gestational age of about 5 to about 20 weeks; b) expanding the at least one stem cell to form an expanded stem cell population; and c) injecting a therapeutically effective amount of the expanded stem cell population to at least one area of the brain of a subject.

2. The method of claim 1 wherein the expanded stem cell population differentiates into neurons that engraft in vivo into the brain of the subject.

3. The method of claim 1, wherein the disease or disorder is caused by cerebral ischemia, hemorrhage, and trauma.

4. The method of claim 3, wherein the disease or disorder involves paralysis, speech impairment, loss of memory, or reasoning ability.

5. The method of claim 3, wherein the disease or disorder involves motor dysfunction or cognitive deficit.

6. The method of claim 1, wherein expanding the at least one neural stem cell includes culturing the neural stem cell in absence of serum.

7. The method of claim 1, wherein expanding the at least one stem cell to form an expanded stem cell population is conducted in the absence of LIF.

8. The method of claim 1, wherein expanding the at least one neural stem cell includes exposing the at least one neural stem cell to at least one growth factor.

9. The method of 8, wherein the growth factor is selected from the group consisting of bFGF, EGF, TGF-alpha, aFGF and combinations thereof.

10. The method of claim 1, wherein at least 30% of the expanded stem cell population is capable of generating neurons in brain tissue of the subject.

11. The method of claim 1, wherein at least 50% of the expanded stem cell population is capable of differentiating into neurons in vitro.

12. The method of claim 1, wherein the at least one area of the brain includes cerebral hemispheres, cerebral cortex, subcortex motor cortex, striatum, internal capsule, thalamus, hypothalamus, hippocampus, midbrain, brainstem, and cerebellum.

13. The method of claim 1, wherein the subject experienced an event that caused cerebral ischemia.

14. The method of claim 13, wherein the event is a stroke.

15. A method of inhibiting or relieving stroke in a subject in need thereof, said method comprising: a) isolating at least one neural stem cell from spinal cord tissue of a human having a gestational age of about 5 to about 20 weeks; b) expanding in vitro said neural stem cell to form an expanded population; c) concentrating the expanded population; and d) introducing a therapeutically effective amount of said expanded population to at least one area of the subject brain.

16. The method of claim 15 wherein at least 20% of the expanded population is capable of generating neurons in brain tissue of the subject.

17. The method of claim 15, wherein expanding the at least one neural stem cell includes culturing the neural stem cell in absence of serum.

18. The method of claim 15, wherein expanding the at least one stem cell to form an expanded stem cell population is conducted in the absence of LIF.

19. The method of claim 15, wherein expanding the at least one neural stem cell includes exposing the at least one neural stem cell to at least one growth factor.

20. The method of claim 19, wherein the growth factor is selected from the group consisting of bFGF, EGF, TGF-alpha, aFGF and combinations thereof.

21. The method of claim 15, wherein at least 30%, of the expanded population is capable of generating neurons in brain tissue of the subject.

22. The method of claim 15, wherein introducing the therapeutically effective amount of the expanded population includes injecting at least a portion of the therapeutically effective amount into one to a plurality of areas of the recipient brain.

23. The method of claim 22, wherein the areas of the recipient brain include cerebral hemispheres, cerebral cortex, subcortex motor cortex, striatum, internal capsule, thalamus, hypothalamus, hippocampus, midbrain, brainstem, and cerebellum.

* * * * *